US009629967B2

(12) United States Patent
Power et al.

(10) Patent No.: US 9,629,967 B2
(45) Date of Patent: *Apr. 25, 2017

(54) INSUFFLATION SYSTEM

(71) Applicant: Aerosurgical Limited, Dangan, Galway (IE)

(72) Inventors: Patrick Joseph Power, Moycullen (IE); Conor Paul Duffy, Roscahill (IE)

(73) Assignee: Aerosurgical Limited, Dangan, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/473,845

(22) Filed: Aug. 29, 2014

(65) Prior Publication Data
US 2015/0057600 A1    Feb. 26, 2015

Related U.S. Application Data

(63) Continuation of application No. 14/042,516, filed on Sep. 30, 2013, now abandoned, which is a
(Continued)

(51) Int. Cl.
*A61M 13/00* (2006.01)
*A61M 11/00* (2006.01)
(Continued)

(52) U.S. Cl.
CPC ....... *A61M 13/003* (2013.01); *A61B 17/3474* (2013.01); *A61M 11/00* (2013.01);
(Continued)

(58) Field of Classification Search
CPC . A61B 17/3474; A61M 11/00; A61M 11/005; A61M 13/003; A61M 2202/0241;
(Continued)

(56) References Cited

U.S. PATENT DOCUMENTS 5,164,740 A    11/1992  Ivri
5,246,419 A     9/1993  Absten
(Continued)

FOREIGN PATENT DOCUMENTS

EP           0 937 478 A1   8/1999
WO    WO 2004/043274 A1    5/2004
(Continued)

OTHER PUBLICATIONS

International Search Report for PCT/IE2010/000046, published Nov. 19, 2010.

*Primary Examiner* — Imani Hayman
(74) *Attorney, Agent, or Firm* — Bookoff McAndrews, PLLC

(57) ABSTRACT

An aerosol generator is positioned adjacent to a patient as an attachment to a trocar. The trocar has an entry port for insufflation gas. Aerosol generated by a vibrating element is entrained in the insufflation gas and the mixture is delivered through the trocar. The aerosol may contain a medicament. The trocar may be a conventional trocar. Such trocars are typically used for a camera. The delivery of the aerosolized medicament can occur at the start of the procedure and be delivered in bolus. At the start of the procedure, the peritoneum is being inflated by the flow of insufflator gas. This gas flow will help to entrain the aerosolized medicament to the pneumoperitoneum regions. The surgeon can temporarily remove the camera from the trocar port to facilitate insertion and positioning of the aerosolizing unit.

22 Claims, 38 Drawing Sheets

Related U.S. Application Data continuation of application No. 13/370,003, filed on Feb. 9, 2012, now Pat. No. 8,551,036, which is a continuation-in-part of application No. 12/853,538, filed on Aug. 10, 2010, now abandoned.

(60) Provisional application No. 61/232,512, filed on Aug. 10, 2009, provisional application No. 61/440,946, filed on Feb. 9, 2011.

(51) Int. Cl.
*A61B 17/34* (2006.01)
*B05B 12/08* (2006.01)
*B05B 17/00* (2006.01)
*B05B 17/06* (2006.01)

(52) U.S. Cl.
CPC ... *A61M 11/005* (2013.01); *A61M 2202/0241* (2013.01); *A61M 2205/3327* (2013.01); *A61M 2205/3334* (2013.01); *A61M 2205/50* (2013.01); *A61M 2205/8206* (2013.01); *B05B 12/081* (2013.01); *B05B 17/0646* (2013.01); *B05B 17/0669* (2013.01)

(58) Field of Classification Search
CPC .. A61M 2205/3327; A61M 2205/3334; A61M 2205/50; A61M 2205/8206; B05B 12/081; B05B 17/0646; B05B 17/0669
See application file for complete search history.

(56) References Cited

U.S. PATENT DOCUMENTS

| | | |
|---|---|---|
| 5,586,550 A | 12/1996 | Ivri et al. |
| 5,758,637 A | 6/1998 | Ivri et al. |
| 5,938,117 A | 8/1999 | Ivri |
| 6,014,970 A | 1/2000 | Ivri et al. |
| 6,085,740 A | 7/2000 | Ivri et al. |
| 6,540,154 B1 | 4/2003 | Ivri et al. |
| 6,546,927 B2 | 4/2003 | Litherland et al. |
| 6,845,770 B2 | 1/2005 | Klimowicz et al. |
| 2005/0021766 A1 | 1/2005 | McKeowen et al. |
| 2009/0192444 A1 | 7/2009 | Albrecht et al. |

FOREIGN PATENT DOCUMENTS

| | | |
|---|---|---|
| WO | WO 2005/092264 A1 | 10/2005 |
| WO | WO 2008/117264 A1 | 10/2008 |

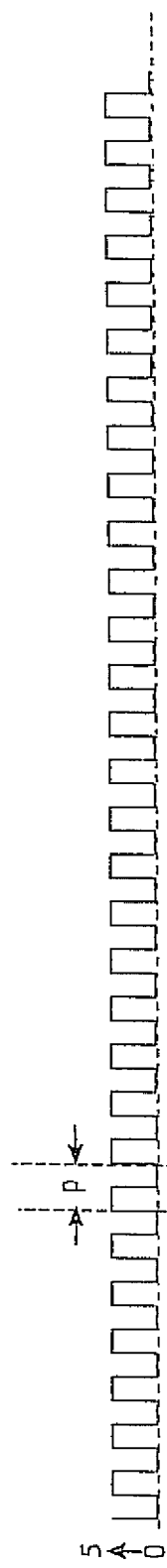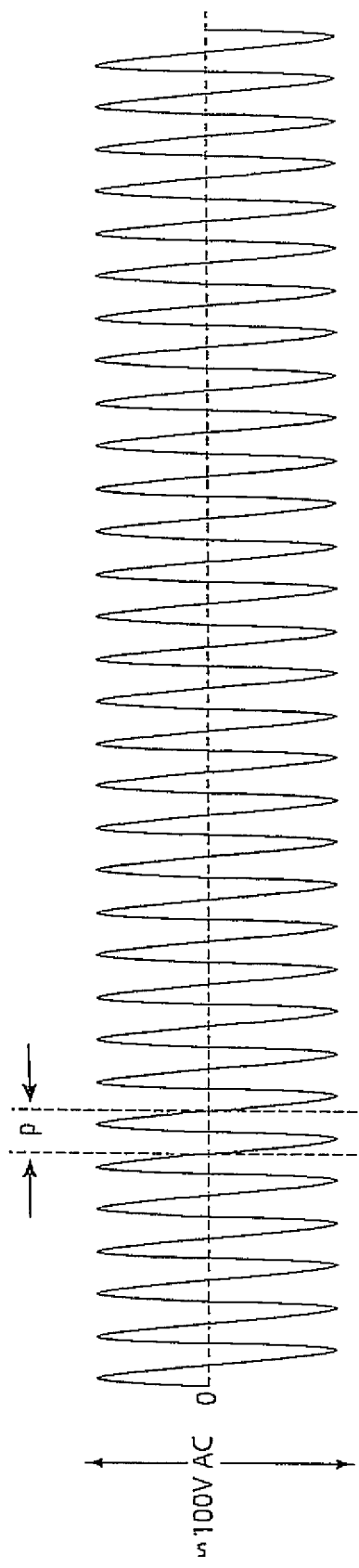

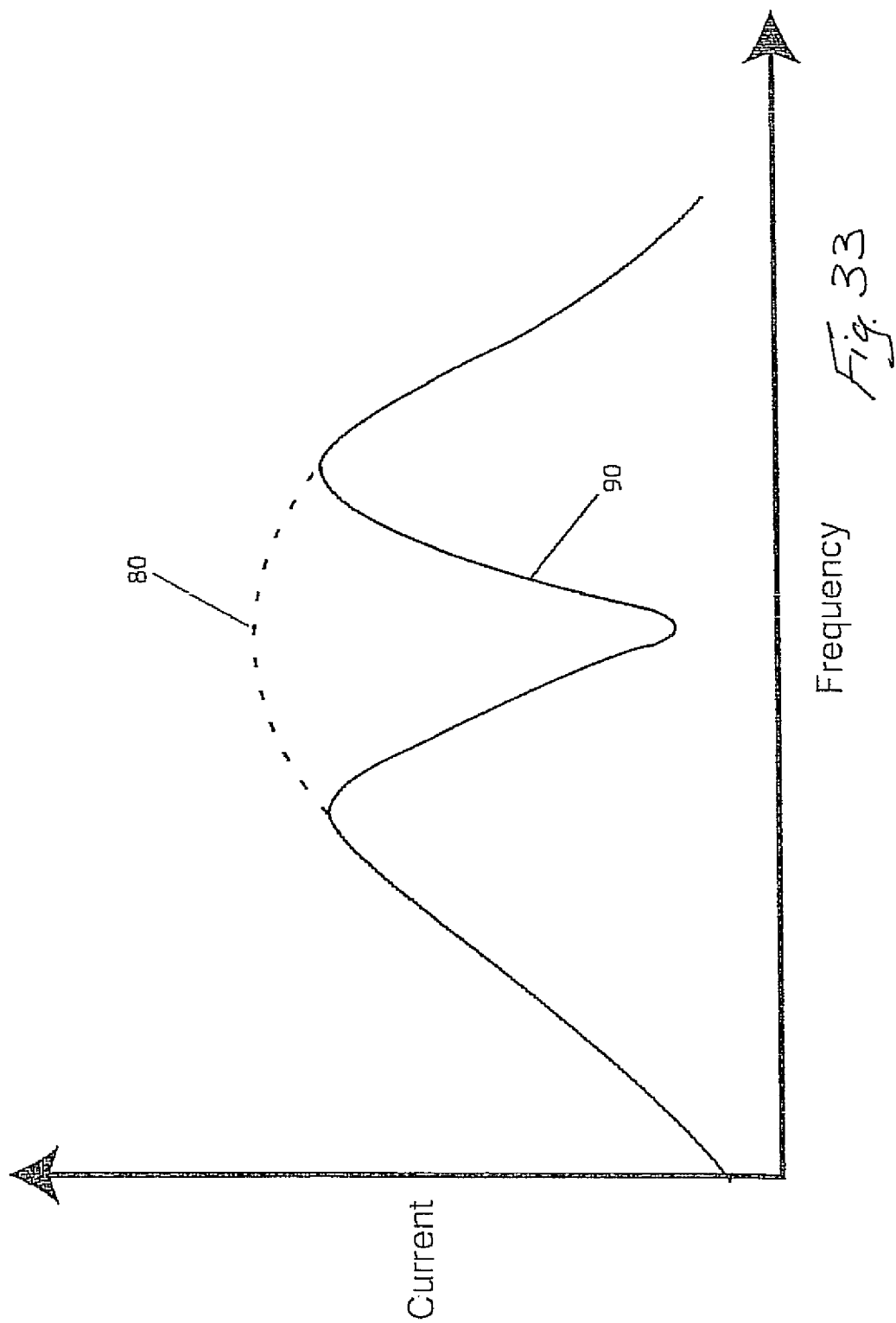

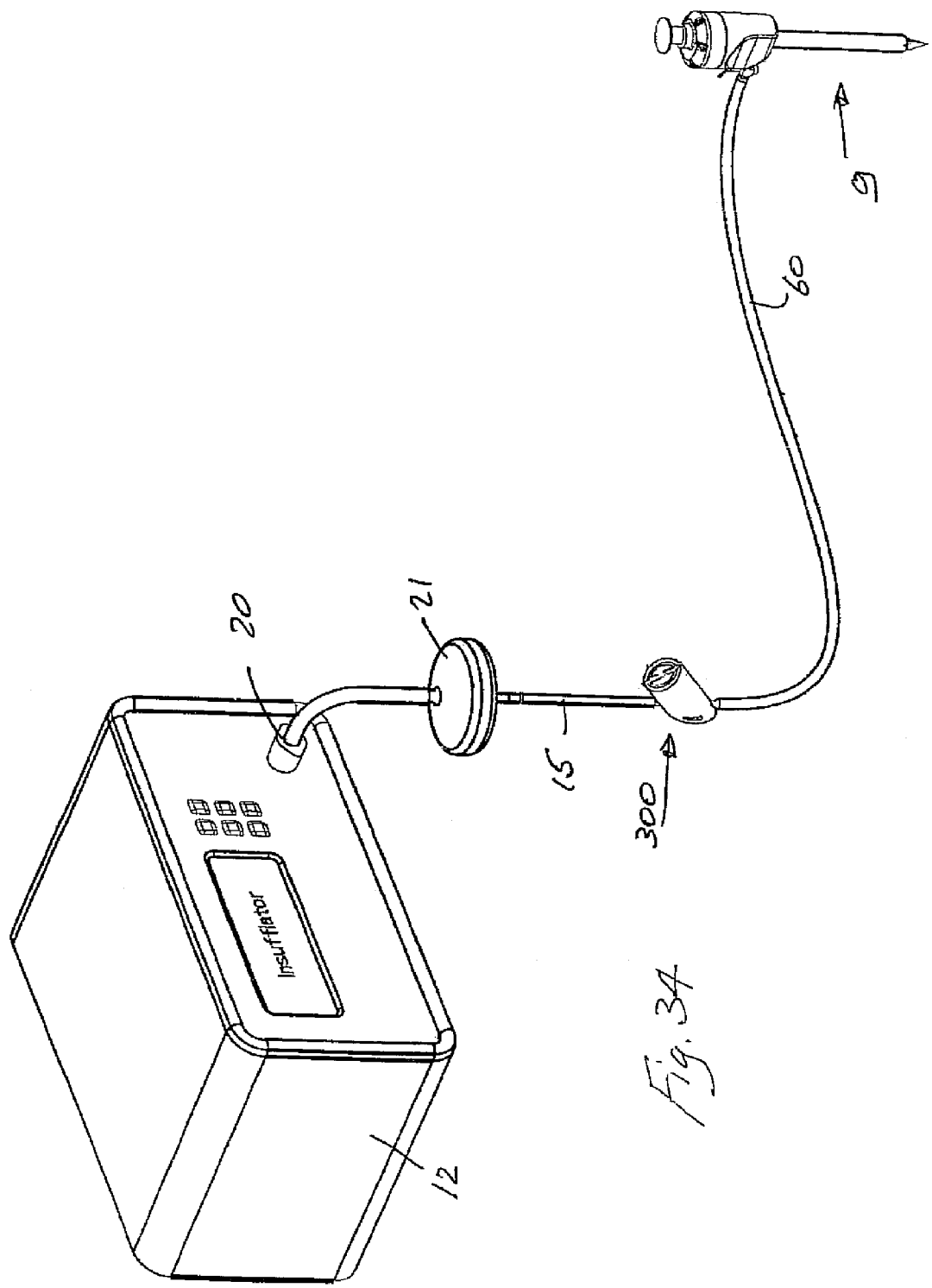

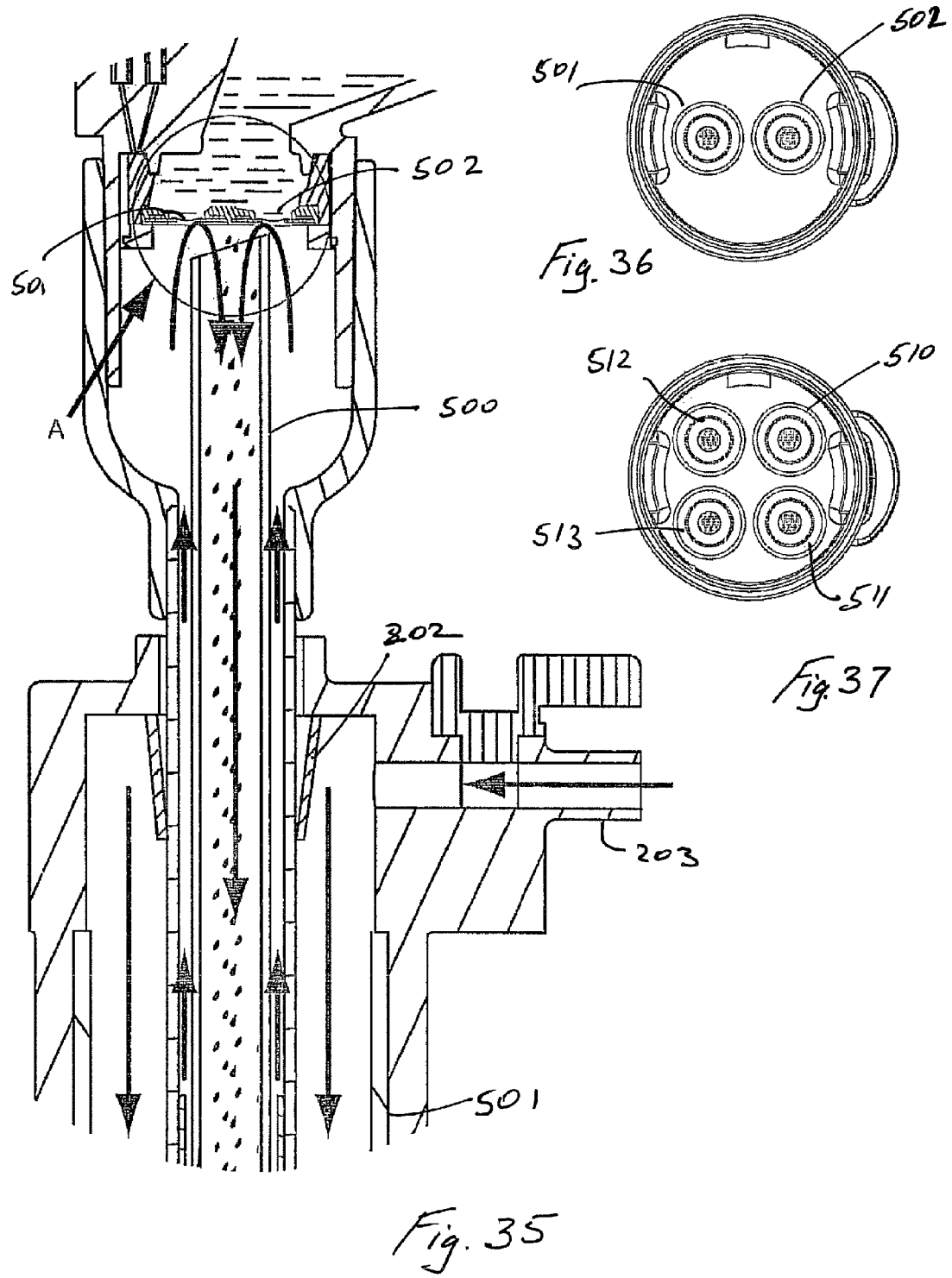

INSUFFLATION SYSTEM

CROSS-REFERENCE TO RELATED APPLICATIONS

The present application is a continuation of U.S. patent application Ser. No. 14/042,516, filed Sep. 30, 2013, now abandoned, which is a continuation of U.S. patent application Ser. No. 13/370,003, filed Feb. 9, 2012, now U.S. Pat. No. 8,551,036, which claims the benefit of U.S. Provisional Application No. 61/440,946, filed Feb. 9, 2011, and is a continuation-in-part of U.S. patent application Ser. No. 12/853,538, filed Aug. 10, 2010, now abandoned, which claims the benefit of U.S. Provisional Application No. 61/232,512, filed Aug. 10, 2009. The disclosure of each of these applications is incorporated herein in its entirety by reference thereto.

BACKGROUND

Laparoscopic surgery, also called minimally or less invasive surgery (MIS or LIS) or keyhole surgery is a modern surgical technique in which operations in the body are performed through small incisions as compared to the larger incisions needed in traditional surgical procedures. Gas such as carbon dioxide is delivered, via an insufflator, into a body cavity such as the abdomen leading to the formation of a pneumoperitoneum, thereby providing sufficient space for the surgeon to operate. The insufflator maintains the pneumoperitoneum and acts to renew the gas when leaks occur.

Gas, such as, for example, carbon dioxide, that is used for insufflation is both cold and dry and it is not surprising therefore those patients undergoing laparoscopic procedures often suffer a significant drop in core body temperature, which can result in considerable post-surgical pain and significant complications, such as cardiac stress, immunological and clotting problems, for the patient. By using standard thermo physical principles it has been shown that the major cause of patient heat loss is due to evaporation from the body acting to humidify the large volumes of dry insufflated gas at ATPD (Ambient Temperature Pressure Dry) passing into the body which is at BTPS (Body Temperature Pressure Saturated). If such heat loss could be minimized, post-operative pain and the significant side effects suffered by the patient could be considerably alleviated.

Various attempts have been made to condition insufflation gas by heating, humidifying, and/or filtering the gas. However, in general, known insufflation gas-conditioning systems suffer from one or more disadvantages including complexity of construction involving expensive monitoring devices, inaccurate control, and/or difficulties in using them in a controlled working environment.

Some systems employ heat moisture exchangers (HME). These operate directly in the flow path of the insufflation gas and are therefore inherently susceptible to affecting pressure or flow, dependent upon their level of saturation and condition. Other systems require manual intervention to respond to patients' needs by the adding of moisture. Other devices require the cumbersome procedure of passing gas over and through non-heated or heated liquid containers. Such devices present the major drawback of impeding pressure measurement in the insufflation cavity.

Systems using conventional jet nebulizers or nebulization catheters exhibit one or more of the following disadvantages: impaction of larger particles; fogging in the body cavity thus reducing the surgeon's visibility; and interference with insufflator settings increasing flow/pressure in the system.

The present invention is directed towards providing an insufflation method and apparatus.

Flow of aerosol through long lengths of tubing may lead to increased rainout and loss of suspended aerosol delivered to the pneumoperitoneum. This impacts both effectiveness of the treatment and the time required to deliver any given medication volume.

Standard connections for inflow gas at a Trocar housing tend to be small diameter with sharp 90° changes in flow direction. This may lead to increased rainout and loss of suspended aerosol delivered to the pneumoperitoneum.

Access to the control mechanism for the aerosol generator is generally remote from the patient. This may inconvenience the surgeon where immediate changes in aerosol delivery are required during the course of a procedure.

Delivery of aerosol into the pneumoperitoneum is generally completely dependent on the flow at insufflator. Where the insufflator is providing low flow, aerosol may not be carried into the pneumoperitoneum.

Positioning the aerosol generating element on the tubing circuit between the insufflator and the Trocar presents challenges such are location, need for supporting brackets, and potential to obscure displays on important equipment.

SUMMARY

In accordance with exemplary embodiments of the present invention an apparatus for use in procedures involving insufflation comprises:
  an aerosol generator for aerosolizing a fluid; and
  delivery means such as a delivery tube and/or a trocar for delivery of the aerosol.

In some exemplary embodiments, the aerosol generator is mounted to the trocar. The aerosol generator may be mountable to the trocar. The aerosol generator may be releasably mounted to the trocar.

In some exemplary embodiments, the aerosol generator is integral with the trocar.

The trocar may comprise an entry port for insufflation gas. The apparatus may comprise means for entraining aerosol with an insufflation gas for delivery of the insufflation gas with entrained aerosol.

In some exemplary embodiments, the trocar comprises a housing having a proximal end to which the aerosol generator is mounted and a distal end through which aerosol is delivered, the trocar having a proximal entry port for insufflation gas, the apparatus comprising an aerosol delivery tub means extending from the aerosol generator into the trocar housing, the aerosol delivery tube having an aerosol outlet which is located distally with respect to the insufflation gas entry port of the trocar.

The aerosol outlet of the aerosol delivery tube may extend into the trocar for a length which is at least 10%, at least 15%, or at least 20% of the length of the trocar.

Preferably there is a proximal seal between the trocar and the aerosol delivery tube.

In some exemplary embodiments, the aerosol delivery tube comprises an entry port for receiving a flow of insufflation gas. The insufflation gas entry port of the aerosol delivery tube may be located proximally of the proximal end of the trocar.

The apparatus in accordance with some exemplary embodiments comprises flow diverting means for delivery of insufflation gas to the insufflation gas entry port of the trocar and/or to the insufflation gas entry port of the aerosol delivery tube.

In some other exemplary embodiments the aerosol delivery tube means comprises an inner tube and an outer tube which are spaced-apart to define an insufflation gas flow path therebetween.

Preferably there is a distal seal between the outer tube and the trocar.

In some exemplary embodiments, the insufflation gas flow path extends into the aerosol delivery chamber for entraining insufflation gas with the aerosol, the insufflation gas with entrained aerosol being delivered through the inner tube and extending from the inner tube into the trocar at the distal end of the tube means.

The distal end of the outer tube may be located proximally with respect to the distal end of the inner tube to define an entry port for insufflation gas.

In some exemplary embodiments, the aerosol generator is located at a proximal end of the trocar.

In some other exemplary embodiments, the aerosol generator is located at a distal end of the trocar. In this case the apparatus may comprise a first delivery means for delivering insufflation gas to a location adjacent to the aerosol generator.

The apparatus may comprise second delivery means for delivery of liquid to be aerosolized to the aerosol generator. The delivery means may comprise a delivery tube extending from a liquid housing to the aerosol generator.

In some exemplary embodiments, the aerosol generator is mounted to an outer tube which extends through the trocar from the liquid housing. A distal end of the outer tube may be located adjacent to a distal end of the trocar.

The aerosol generator may be located adjacent to a distal end of the trocar.

In some exemplary embodiments, the apparatus comprises control means for operation of the aerosol generator, the control means extending through the inner and outer tubes from a proximal end at the liquid housing to a distal end at the aerosol generator.

In some exemplary embodiments, the apparatus comprises an insufflator for generating an insufflation gas.

The apparatus may comprise a controller to control the operation of the aerosol generator. The controller may be remote from the trocar. The controller may be mounted to the trocar. The controller may be mountable to the trocar. The controller may be releasably mounted to the trocar.

In some exemplary embodiments, the controller comprises a first controller local to the trocar and a second controller remote from the trocar.

The controller may be configured to control the flow rate of the fluid to be aerosolized.

In some exemplary embodiments, the controller is configured to deliver different flow rates of aerosol at different stages of a surgical procedure.

In some exemplary embodiments, the controller is configured to deliver full flow at the start and/or end of a procedure.

The controller may be configured to deliver reduced flow during a procedure.

In some exemplary embodiments, the controller is set to deliver a pre-set amount of aerosol into insufflation gas. The apparatus may comprise means for varying the pre-set amount of aerosol. The means for varying the pre-set amount of aerosol may comprise a user interface such as a keypad or switch.

In some other exemplary embodiments, the controller is configured to control operation of the aerosol generator responsive to the insufflation gas. The controller may be configured to control operation of the aerosol generator responsive to the flow rate of the insufflation gas.

In some exemplary embodiments, the aerosol generator comprises a vibratable member having a plurality of apertures extending between a first surface and a second surface. The first surface may be adapted to receive the fluid to be aerosolized. The aerosol generator may be configured to generate an aerosol at the second surface.

In some exemplary embodiments, the vibratable member is dome-shaped in geometry. Alternatively, the vibratable member may comprise a stretched flat shape.

In some exemplary embodiments, the vibratable member comprises a piezoelectric element.

In some exemplary embodiments, the apertures in the vibratable member are sized to aerosolize the first fluid by ejecting droplets of the first fluid such that the majority of the droplets by mass have a size of less than 100 micrometers, less than 50 micrometers.

The apertures in the vibratable member may be sized to aerosolize the first fluid by ejecting droplets of the first fluid such that the majority of the droplets by mass have a size of less than 40 micrometers.

The apertures in the vibratable member may be sized to aerosolize the first fluid by ejecting droplets of the first fluid such that the majority of the droplets by mass have a size of less than 30 micrometers.

The apertures in the vibratable member may be sized to aerosolize the first fluid by ejecting droplets of the first fluid such that the majority of the droplets by mass have a size of less than 20 micrometers. In some exemplary embodiments, a size range band is from 3 to 15 micrometers.

In some exemplary embodiments, the controller is configured to control the pulse rate at a set frequency of vibration of the vibratable member.

The controller may be impedance matched to the aerosol generator.

In some exemplary embodiments, the apparatus comprises means to determine whether the fluid is in contact with the aerosol generator. The determining means may be configured to determine at least one electrical characteristic of the aerosol generator. The determining means may be configured to determine at least one electrical characteristic of the aerosol generator over a range of vibration frequencies.

In some exemplary embodiments, the determining means is configured to compare the at least one electrical characteristic against a pre-defined set of data.

In accordance with exemplary embodiments of the present invention, a method for carrying out a procedure involving insufflation comprises the steps of:
 providing an aerosol generator;
 providing a trocar;
 aerosolizing a fluid using the aerosol generator; and
 delivering the aerosol from the trocar.

In accordance with exemplary embodiments of the present invention, a method of introducing aerosol to a body cavity independent of the flow of insufflation gas is provided.

In some exemplary embodiments, the method comprises:
 generating an insufflation gas; and
 entraining the aerosol with the insufflation gas.

The method may comprise the step of controlling the aerosolization of the fluid.

The method may comprise delivering different flow rates of aerosol at different stages of a surgical procedure. The method may comprise delivering full flow at the start and/or end of a procedure. The method may comprise delivering reduced flow during a procedure. The method comprise delivering a pre-set amount of aerosol into insufflation gas.

In some exemplary embodiments, the method comprises the step of delivering the entrained fluid and insufflation gas into the body to insufflate at least part of the body.

In some exemplary embodiments, the fluid is an aqueous solution.

In some exemplary embodiments, the aqueous solution is saline having a salt concentration of greater than 1 µM.

In some exemplary embodiments, the fluid contains a therapeutic and/or prophylactic agent.

The agent may be one or more selected from the group comprising an analgestic, an anti-inflammatory, an anti-infective, an anaesthetic, an anticancer chemotherapy agent, and an anti-adhesion agent.

In some exemplary embodiments, the procedure is a laparascopic procedure.

In accordance with exemplary embodiments of the present invention, an apparatus for use in procedures involving insufflation comprises:
an aerosol generator for aerosolizing a fluid,
a trocar for delivery of the aerosol, the trocar comprising a housing to which the aerosol generator is mounted, the trocar having a proximal entry part for insufflation gas and a distal end through which aerosol is delivered, the apparatus comprising an aerosol delivery tube extending from the aerosol generator into the trocar housing, the aerosol delivery tube having an aerosol outlet which is located distally with respect to the insufflation gas entry port of the trocar.

In some exemplary embodiments, a proximal end of the aerosol delivery tube is located adjacent to the aerosol generator.

In some exemplary embodiments, the apparatus is adapted to direct insufflation gas from the trocar insufflation gas entry port to a proximal end of the aerosol delivery tube for entraining the aerosol in the insufflation gas and delivery of the insufflation gas and entrained aerosol through the trocar.

A gap may be provided between the aerosol delivery tube and the aerosol generator for delivery of insufflation gas into the aerosol delivery tube at the proximal end thereof.

In an exemplary case the gap is defined by an angled cut at the proximal end of the aerosol delivery tube. The angle cut may be less than 20°, less than 15°, less than 10°. In one embodiment the angle cut is approximately 5°.

There may be a proximal seal between the trocar and the aerosol delivery tube.

The aerosol delivery tube means may comprise an inner tube and an outer tube which are spaced-apart to define an insufflation gas flow path therebetween. There may be a distal seal between the outer tube and the trocar.

The trocar systems of the present invention may be adapted to accommodate two or more aerosol generators. Such systems with more than one aerosol generator increases nebulizer output and reduces the time required to deliver a required amount of aerosol.

In some exemplary embodiments, there is a seal between the distal end of a trocar insert the trocar to prevent insufflation gas from passing between the outer wall of the insert and the inner wall of the trocar. The seal may comprise a bulbous region at the distal end of the insert which is an interference fit in the shaft of the trocar. This arrangement facilitates ease of insertion and removal of the trocar insert whilst maintaining a seal when the insert is in place in the trocar.

There may be any desired number of aerosol generators.

In some exemplary embodiments, a trocar insert has a shortened length L which is sufficient to create a seal between the trocar insert and the inner surface of the trocar. Typically the length L is between 30 mm and 65 mm. By reducing the distance the distance to be travelled by the aerosol within the narrow trocar insert the quantity of aerosol exiting the trocar is increased.

In some exemplary embodiments, an inner tube of a trocar insert is extended to a position close to the underside of an aerosol generator. This has the benefit of channelling the flow of generated aerosol for delivery to a patient. This feature may be used with any length of trocar insert. Many different arrangements are possible. There may be a small gap, a tapered interface, an interface with castellations, a single gas inlet slit, and/or dual offset slits to promote vortex formation.

In some exemplary embodiments, an aerosol insert has a modified interface between a proximal end of an inner tube of the insert and an aerosol generator. In some exemplary embodiments, the inner tube comes into contact with the aerosol generator. The inner tube may have an inlet for insufflation gas which is spaced below the proximal end of the inner tube. This modifies the aerosol flow dynamics for improved aerosol delivery efficiency.

A liquid reservoir for the aerosol generator may be modified to facilitate efficient nebulization through a wide range of angles of orientation such as would be encountered in use during laparoscopic surgery. In some exemplary embodiments, a reservoir is tapered. The reservoir may be fitted with a removable plug. The plug may, for example, be of silicon.

In accordance with exemplary embodiments of the present invention, a trocar having an aerosol generator includes a valve such as a flap valve to facilitate the insertion of an instrument such as a trocar blade or obdurator. As the instrument is inserted, the flap valve moves to protect the aerosol generator. When the instrument is not present the flap returns to a rest position and assists in directing the flow of aerosol generated by the aerosol generator down the shaft of the trocar.

Further features and aspects of example embodiments of the present invention are described in more detail below with reference to the appended Figures.

BRIEF DESCRIPTION OF THE DRAWINGS

FIGS. 26 and 27 are graphs of DC voltage versus time and AC voltage versus time respectively to achieve a 100% aerosol output.

—FIG. 28 illustrates the waveform output from a microprocessor to a drive circuit and FIG. 29 illustrates the waveform output from a drive circuit to a nebulizer.

—FIG. 30 illustrates the waveform output from a microprocessor to a drive circuit and FIG. 31 illustrates the waveform output from a drive circuit to a nebulizer.

FIG. 33 is a graph of frequency versus current for another apparatus in accordance with the present invention.

FIG. 34 is a perspective view of another apparatus in accordance with the present invention.

FIG. 35 is an elevational view of portion of another apparatus in accordance with the present invention for use in a procedure involving insufflation of a body cavity, such as laparoscopic surgery.

FIG. 36 is a top plan view of the apparatus of FIG. 35.

FIG. 37 is a plan view of another apparatus in accordance with the present invention.

DETAILED DESCRIPTION

Figure 1:
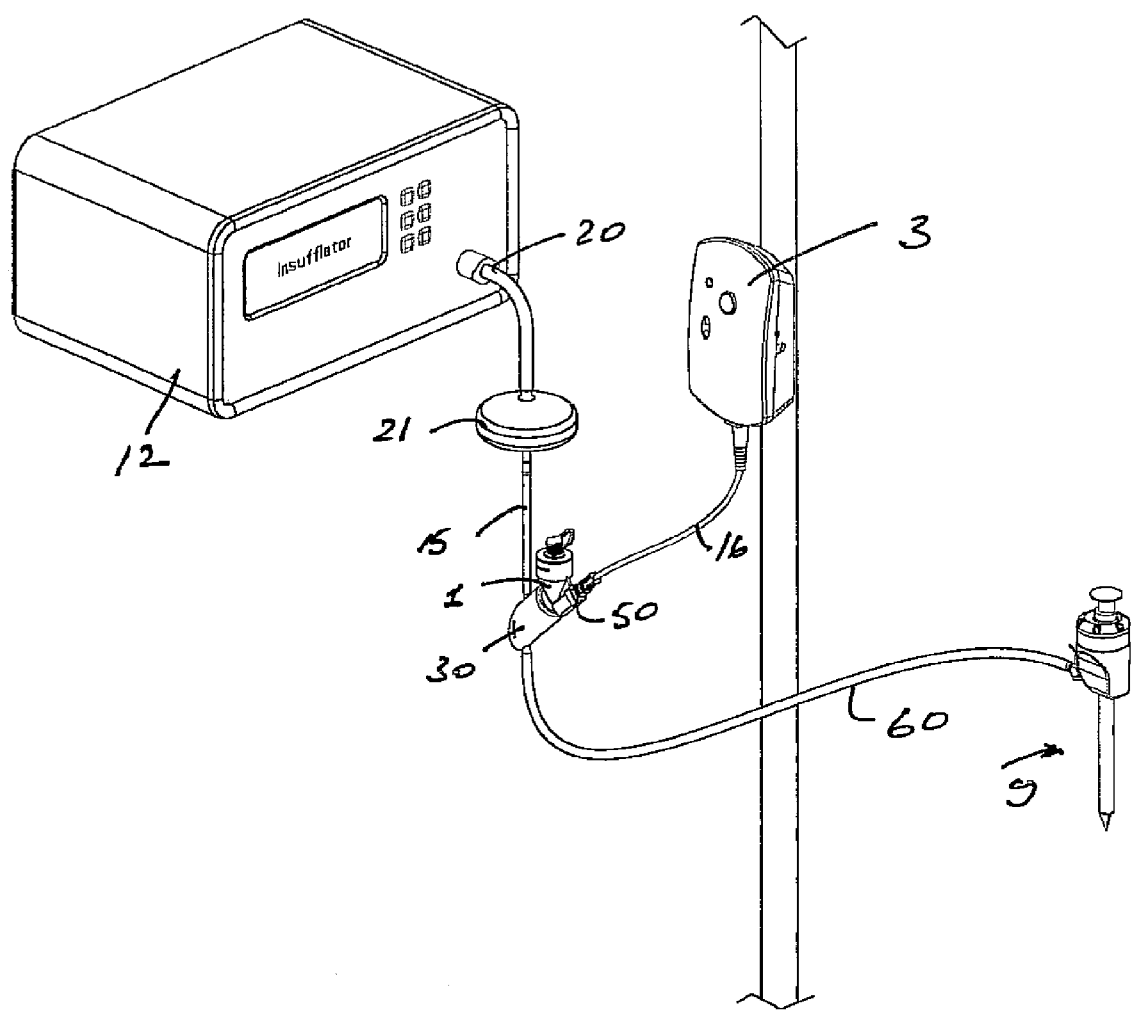
FIG. 1 is a perspective view of an apparatus in accordance with the present invention for use in a procedure involving insufflation of a body cavity, such as laparoscopic surgery.

Referring to FIG. 1 there is illustrated an apparatus in accordance with the present invention for use in insufflation of a body cavity. One such application is laparoscopic surgery. The device is also suitable for use in any situation involving insufflation of a body cavity such as in arthroscopies, pleural cavity insufflation (for example during thoracoscopy), retroperitoneal insufflations (for example retroperitoneoscopy), during hernia repair, during mediastinoscopy and any other such procedure involving insufflation.

The apparatus comprises a reservoir 1 for storing an aqueous solution, an aerosol generator 2 for aerosolizing the solution, and a controller 3 for controlling operation of the aerosol generator 2. In the present invention aerosolized aqueous solution is entrained with insufflation gas. The gas is any suitable insufflation gas such as carbon dioxide. Other examples of suitable insufflation gases are nitrogen, helium, and xenon.

The insufflation gas is delivered into an insufflation gas tubing 15 by an insufflator 12. The insufflator 12 may be of any suitable type such as those available from Karl Storz, Olympus, and Stryker. The insufflator 12 has an outlet 20 through which insufflation gas is delivered. A bacterial filter 21 may be provided within the insufflator or, as illustrated, downstream of the insufflator outlet 20.

Sterile water may be used. In the case of an aqueous solution, any suitable solution may be used. Solutions with a salt concentration in the range 1 µM (micro molar) to 154 mM (milli molar) (0.9% saline) are optimum as they cover the majority of medical applications. In addition, such saline concentrations can be readily nebulized using the aerosolization technology used in the present invention.

Liquid, saline or water for humidifying purposes only and/or medicament, can be delivered into the nebulizer reservoir through the opening in the top of the nebulizer that is appropriately sized to receive standard nebules or alternatively may be applied by syringe or other delivery means. In another exemplary embodiment it would be possible to supply the nebulizer pre-loaded with medicament avoiding the requirement to separately add medicament to the system.

Aqueous solution may be stored in the reservoir 1 container of the nebulizer.

The apparatus comprises an aerosol supply conduit 34 for delivering the aerosol from the aerosol generator 2 into the insufflation gas conduit 15 to entrain the aerosol with the insufflation gas, passing through the gas insufflation conduit 15. The entrained aerosol/insufflation gas mixture passes out of the connector 30 through the outlet 32 and is delivered to the body cavity along a line 60 to a trocar 9.

Figure 23:
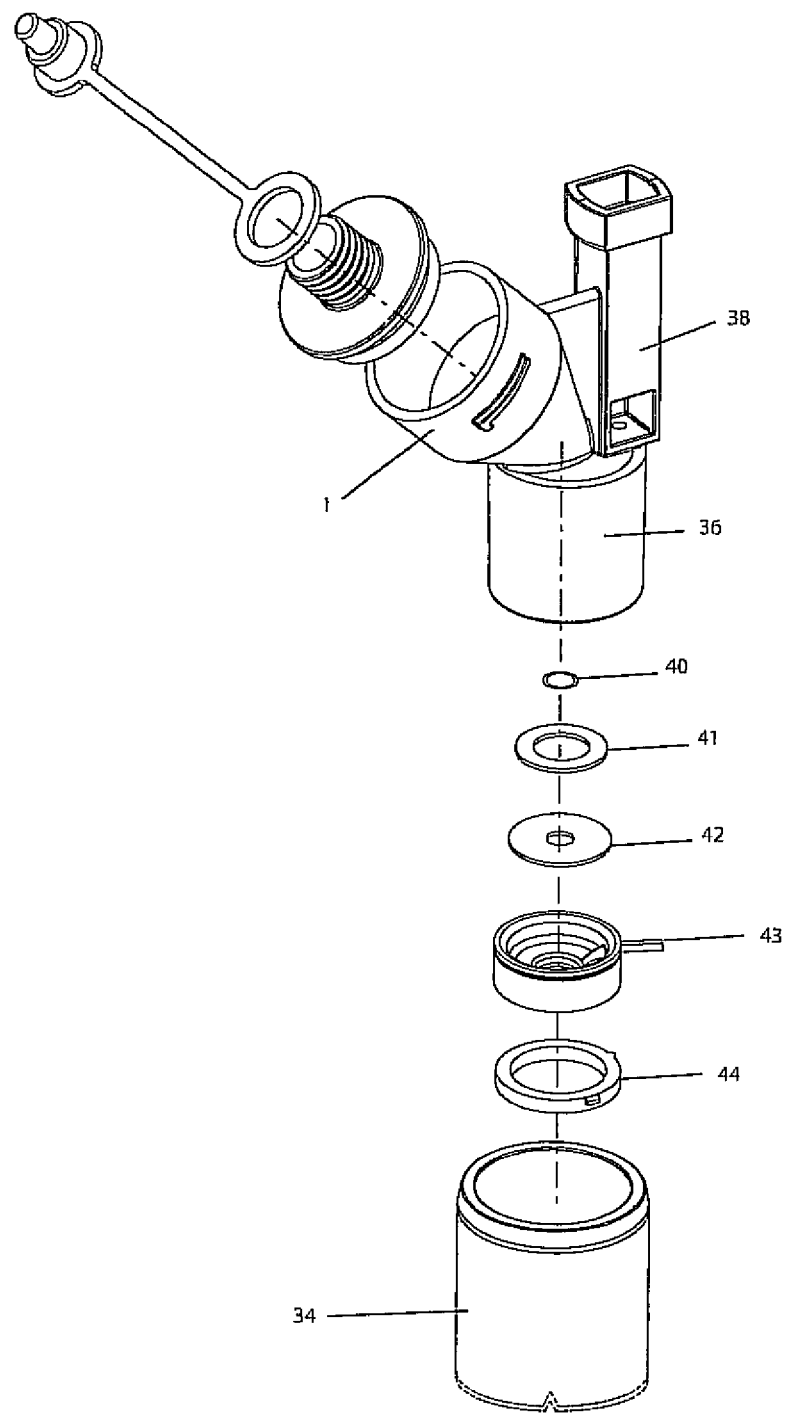
FIG. 23 is an exploded isometric view of an aerosol generator used in the present invention.
Figure 24:
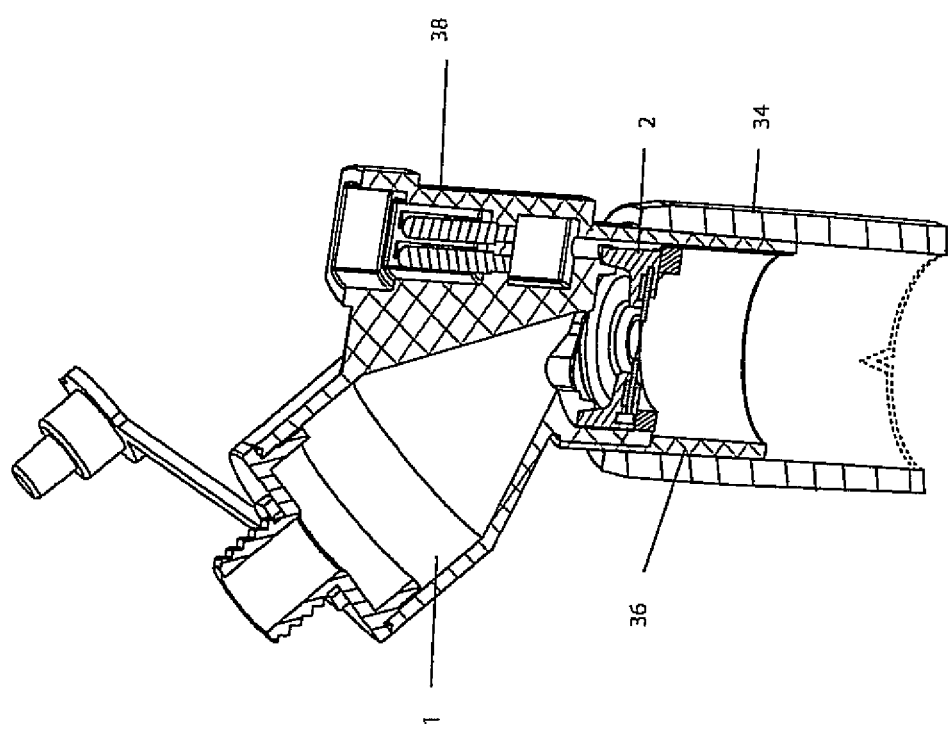
FIG. 24 is a cross-sectional view of the assembled aerosol generator of FIG. 23.

The aerosol supply conduit 34 and the insufflation gas conduit meet at a junction. Referring particularly to FIGS. 23 and 24, in the assembled apparatus the aerosol supply conduit 34 may be releasably mounted to a neck 36 of the aerosol generator housing by means of a push-fit arrangement. This enables the conduit 34 to be easily dismounted from the aerosol generator housing 36, for example for cleaning. The neck 36 at least partially lines the interior of the aerosol supply conduit 34.

The nebulizer (or aerosol generator), has a vibratable member which is vibrated at ultrasonic frequencies to produce liquid droplets. Some specific, non-limiting examples of technologies for producing fine liquid droplets is by supplying liquid to an aperture plate having a plurality of tapered apertures extending between a first surface and a second surface thereof and vibrating the aperture plate to eject liquid droplets through the apertures. Such technologies are described generally in U.S. Pat. No. 5,164,740, U.S. Pat. No. 5,938,117, U.S. Pat. No. 5,586,550, U.S. Pat. No. 5,758,637, U.S. Pat. No. 6,014,970, U.S. Pat. No. 6,085,740, and U.S. Pat. Application Publication No. 2005/021766A, the complete disclosures of which are incorporated herein by reference. However, it should be appreciated that the present invention is not limited for use only with such devices.

Various methods of controlling the operation of such nebulizers or aerosol generators are described in U.S. Pat. No. 6,540,154, U.S. Pat. No. 6,845,770, U.S. Pat. No. 5,938,117, and U.S. Pat. No. 6,546,927, the complete disclosures of which are incorporated herein by reference.

In use, the liquid to be aerosolized is received at the first surface, and the aerosol generator 2 generates the aerosolized first fluid at the second surface by ejecting droplets of the first fluid upon vibration of the vibratable member. The apertures in the vibratable member are sized to aerosolize the liquid by ejecting droplets of the liquid such that the majority of the droplets by mass have a size of less than 5 micrometers. The vibratable member 40 could be non-planar, and may be dome-shaped in geometry.

Referring particularly to FIGS. 23 and 24, in an exemplary case the aerosol generator 2 comprises a vibratable member 40, a piezoelectric element 41 and a washer 42, which are sealed within a silicone overmold 43 and secured in place within the housing 36 using a retaining ring 44. The vibratable member 40 has a plurality of tapered apertures extending between a first surface and a second surface thereof.

The first surface of the vibratable member 40, which in use faces upwardly, receives the liquid medicament from the reservoir 1 and the aerosolized medicament, is generated at the second surface of the vibratable member 40 by ejecting droplets of medicament upon vibration of the member 40. In use, the second surface faces downwardly. In an exemplary case, the apertures in the vibratable member 40 may be sized to produce an aerosol in which the majority of the droplets by weight have a size of less than 5 micrometers.

The complete nebulizer may be supplied in sterile form, which is a significant advantage for a surgical device.

Figure 22:
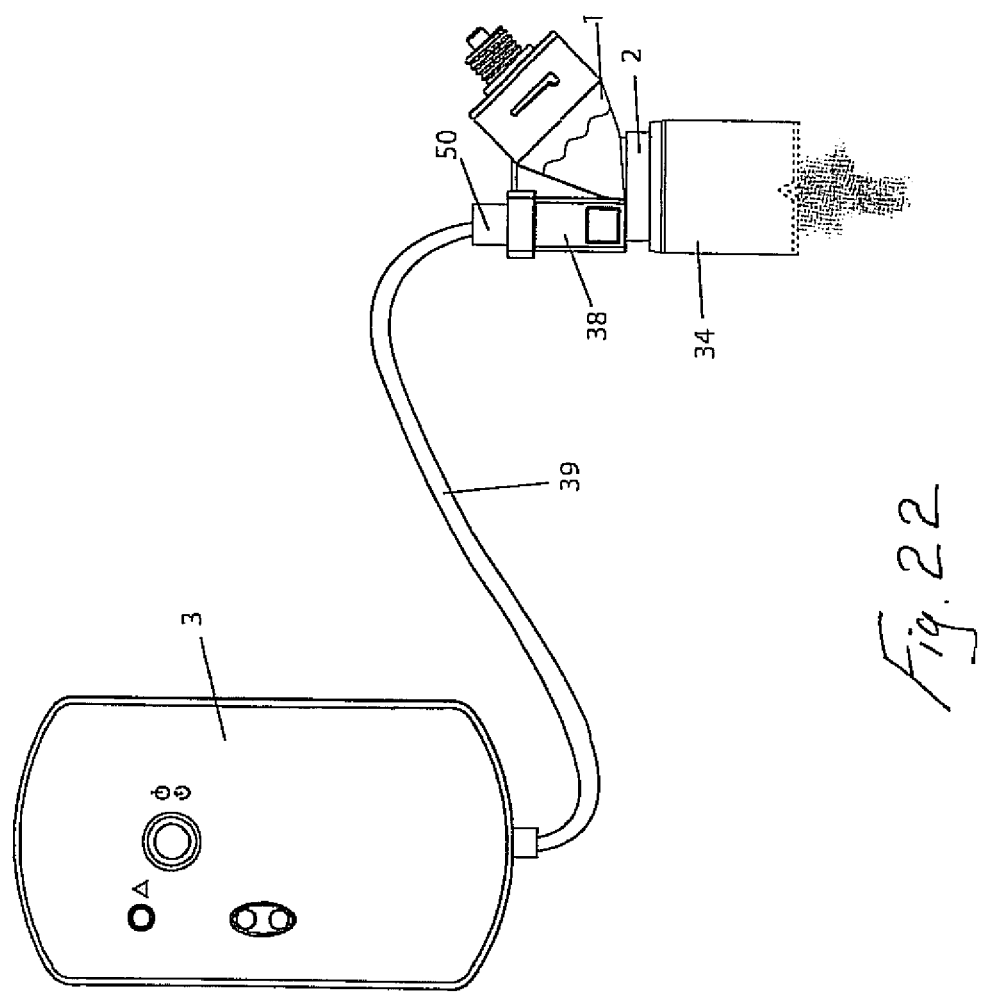
FIG. 22 is a schematic illustration of a part of the apparatus of FIG. 21.

Referring particularly to FIG. 22, the controller 3 controls operation of and provides a power supply to the aerosol generator 2. The aerosol generator has a housing which defines the reservoir 1. The housing has a signal interface port 38 fixed to the lower portion of the reservoir 1 to receive a control signal from the controller 3. The controller 3 may be connected to the signal interface port 38 by means of a control lead 39 which has a docking member 50 for mating with the port 38. A control signal and power may be passed from the controller 3 through the lead 39 and the port 38 to the aerosol generator 2 to control the operation of the aerosol generator 2 and to supply power to the aerosol generator 2 respectively.

The power source for the controller 3 may be an on-board power source, such as a rechargeable battery, or a remote power source, such as a mains power source, or an insufflator power source. When the remote power source is an AC mains power source, an AC-DC converter may be connected between the AC power source and the controller 3. A power connection lead may be provided to connect a power socket of the controller 3 with the remote power source.

Figure 25:
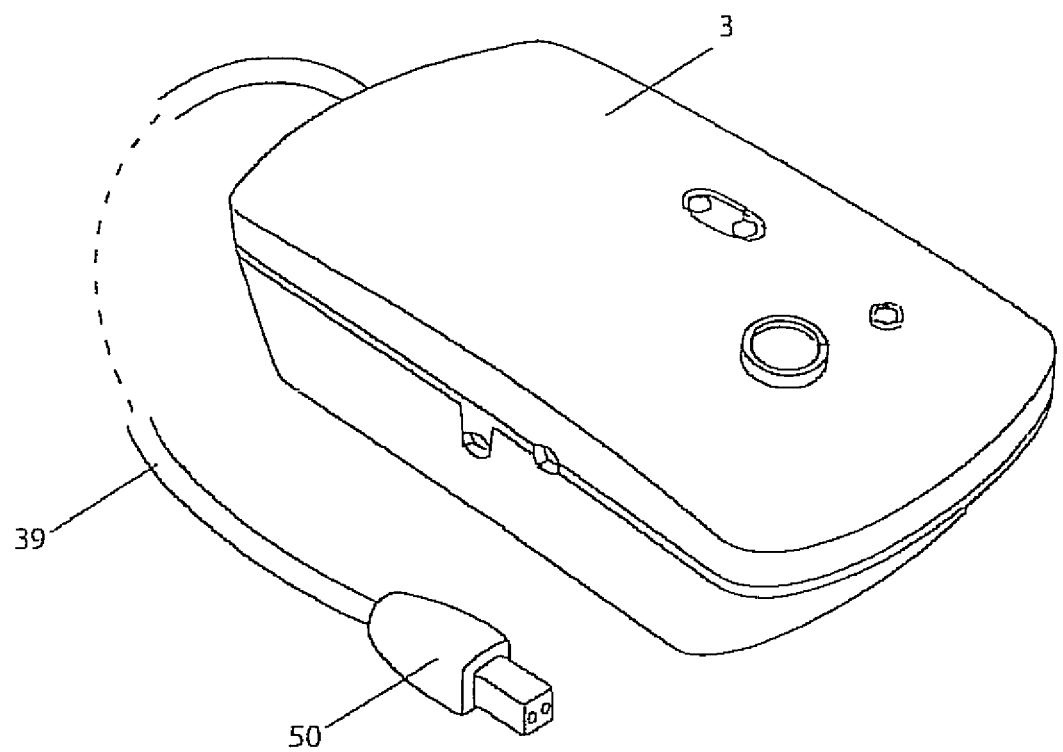
FIG. 25 is a perspective view of a controller housing used in the apparatus of the present invention.

Referring particularly to FIG. 25, the controller 3 has a housing and a user interface to selectively control operation of the aerosol generator 2. Preferably the user interface is provided on the housing which, in use, is located remote from the aerosol generator housing. The user interface may be in the form of, for example, an on-off button. In some embodiments a button may be used to select pre-set values for simplicity of use. In some embodiments a dial mechanism may be used to select from a range of values from 0-100%.

Status indication means are also provided on the housing to indicate the operational state of the aerosol generator 2. For example, the status indication means may be in the form of two visible LEDs, with one LED being used to indicate power and the other LED being used to indicate aerosol delivery. Alternatively, one LED may be used to indicate an operational state of the aerosol generator 2, and the other LED may be used to indicate a rest state of the aerosol generator 2.

A fault indicator may also be provided in the form of an LED on the housing. A battery charge indicator in the form of an LED may be provided at the side of the housing.

The controller 3 may be activated to supply power and a control signal to the aerosol generator 2, which causes the piezoelectric element 41 to vibrate the non-planar member 40. This vibration of the non-planar member 40, causes the aqueous solution at the top surface of the member 40 to pass through the apertures to the lower surface where the aqueous solution is aerosolized by the ejection of small droplets of solution.

Referring particularly to FIGS. 23 and 24, the aerosol passes from the aerosol generator 2 into the neck 36 of the aerosol generator housing, which is mounted within the aerosol supply conduit 34. The aerosol is entrained in the insufflation gas conduit with gas. The entrained mixture of the aerosol and the insufflation gas then passes via an insufflator line 60 to a trocar 9, for example into the abdomen of the patient.

In use during laparoscopic surgery, the flow of the insufflation gas into the abdomen of a patient is commenced to insufflate the abdomen. The controller 3 commences operation of the aerosol generator 2 to aerosolize the aqueous solution. The aerosolized aqueous solution is entrained with the insufflation gas, and delivered through the trocar 9 into the abdomen of the patient to insufflate at least part of the abdomen.

In the event of alteration of the fluid flow rate of the insufflation gas a flow rate sensor/meter may determine the alteration, and the controller 3 alters the pulse rate of the vibratable member of the nebulizer accordingly.

The controller 3 may be configured to control operation of the aerosol generator 2, responsive to the fluid flow rate of the insufflation gas and/or also independent of the fluid flow rate of the insufflation gas.

In an exemplary case, the controller 3 is configured to control operation of the aerosol generator 2 by controlling the pulse rate at a set frequency of vibration of the vibratable member, and thus controlling the fluid flow rate of the aqueous solutions.

Figure 21:
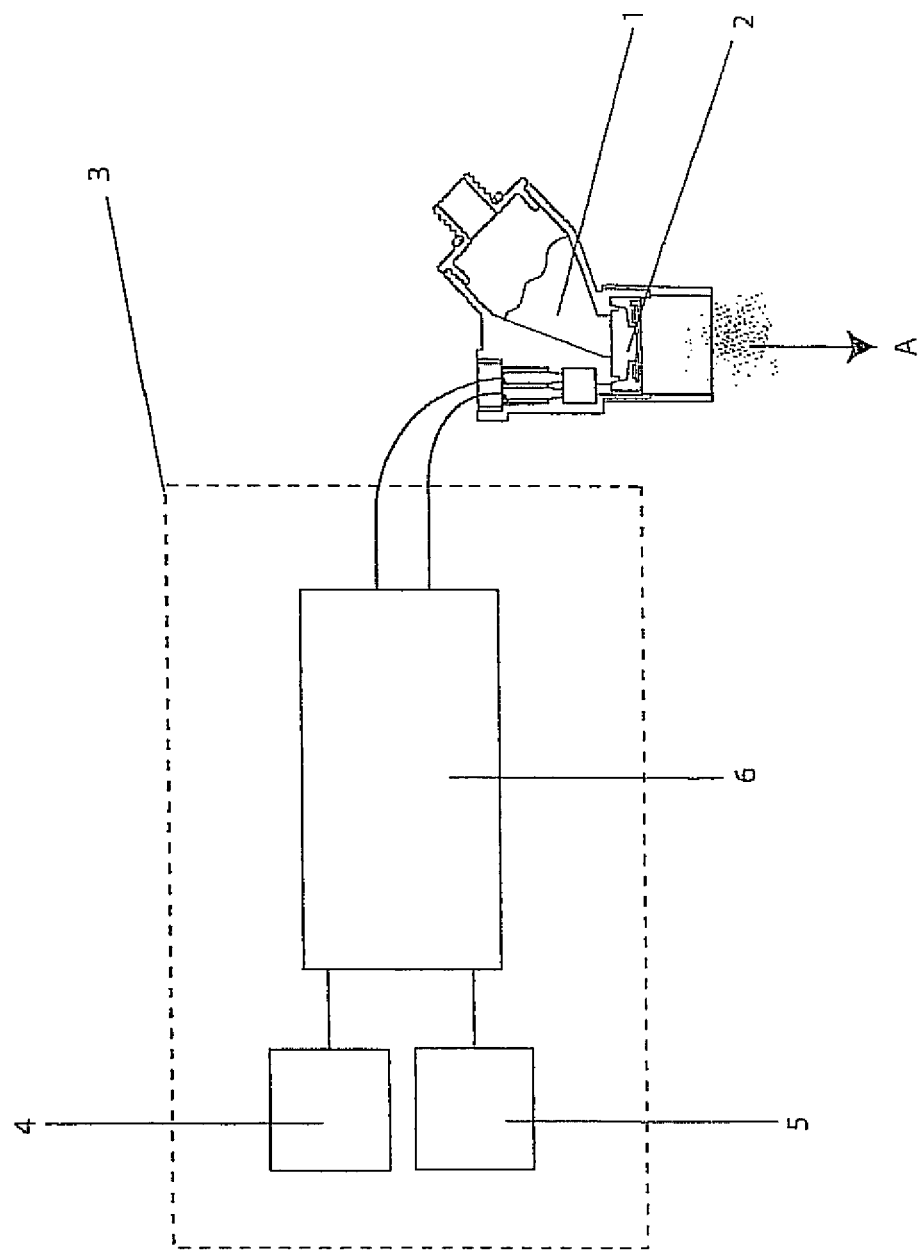
FIG. 21 is a schematic illustration of a part of an apparatus in accordance with the present invention.

The controller 3 may comprise a microprocessor 4, a boost circuit 5, and a drive circuit 6. FIG. 21 illustrates the microprocessor 4, the boost circuit 5, the drive circuit 6 comprising impedance matching components (inductor), the nebulizer 2, and the aerosol. The inductor impedance is matched to the impedance of the piezoelectric element of the aerosol generator 2. The microprocessor 4 generates a square waveform of 128 KHz which is sent to the drive circuit 6. The boost circuit 5 generates a 12V DC voltage required by the drive circuit 6 from an input of either a 4.5V battery or a 9V AC/DC adapter. The circuit is matched to the impedance of the piezo ceramic element to ensure enhanced energy transfer. A drive frequency of 128 KHz is generated to drive the nebulizer at close to its resonant frequency so that enough amplitude is generated to break off droplets and produce the aerosol. If this frequency is chopped at a lower frequency such that aerosol is generated for a short time and then stopped for a short time, this gives good control of the nebulizer's flow rate. This lower frequency is called the pulse rate.

The drive frequency may be started and stopped as required using the microprocessor 4. This allows for control of flow rate by driving the nebulizer 2 for any required pulse rate. The microprocessor 4 may control the on and off times to an accuracy of milliseconds.

The nebulizer 2 may be calibrated at a certain pulse rate by measuring how long it takes to deliver a know quantity of solution. There is a linear relationship between the pulse rate and the nebulizer flow rate. This allows for accurate control over the delivery rate of the aqueous solution.

The nebulizer drive circuit includes or consists of the electronic components designed to generate output sine waveform of approximately 100V AC which is fed to nebulizer 2 causing aerosol to be generated. The nebulizer drive circuit 6 uses inputs from microprocessor 4 and boost circuit 5 to achieve its output. The circuit is matched to the impedance of the piezo ceramic element to ensure good energy transfer.

The aerosol generator 2 may be configured to operate in a variety of different modes, such as continuous, and/or phasic, and/or optimised.

For example, referring to FIG. 26, a 5V DC square waveform output from the microprocessor 4 to the drive circuit 6. FIG. 27 shows a low power, ~100V AC sine waveform output from drive circuit 6 to nebulizer 2 is illustrated. Both waveforms have a period p of 7.8 µS giving them a frequency of 1/7.8 µs which is approximately 128 KHz. Both waveforms are continuous without any pulsing. The aerosol generator may be operated in this mode to achieve 100% aerosol output.

Figure 28:
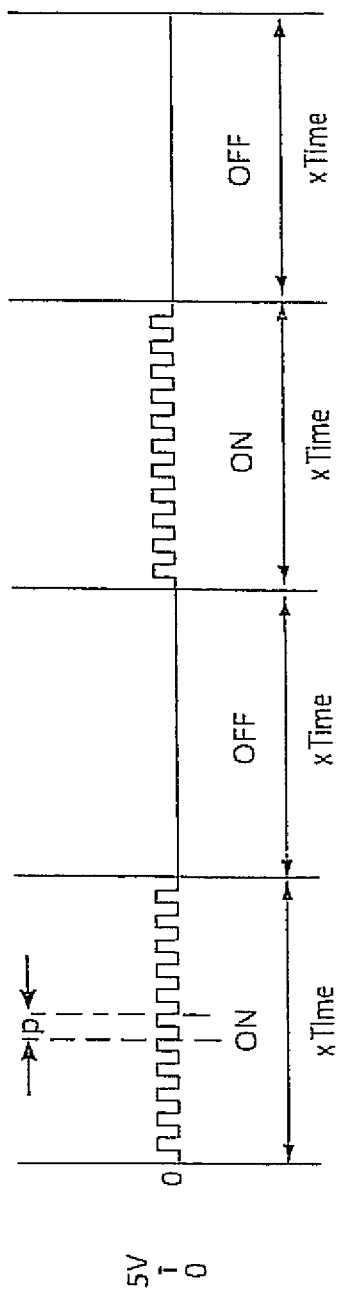
FIGS. 28 and 29 are graphs of DC voltage versus time and AC voltage versus time respectively to achieve a 50% aerosol output
Figure 29:
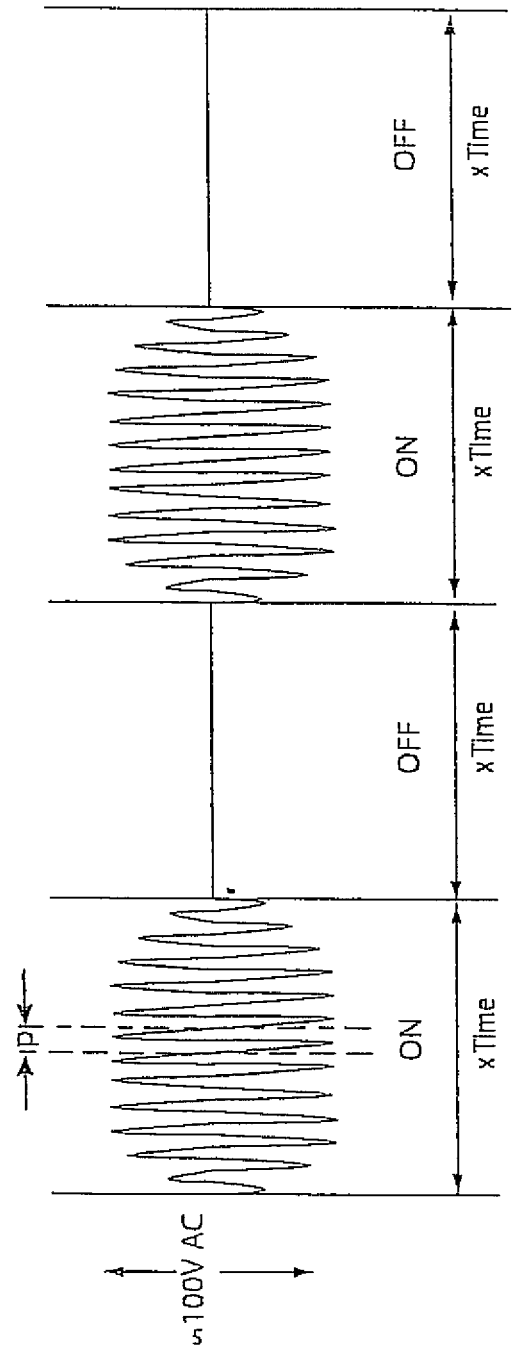

Referring to FIG. 28 in another example, there being illustrated a 5V DC square waveform output from the microprocessor 4 to the drive circuit 6. FIG. 29 shows a low power, ~100V AC sine waveform output from the drive circuit 6 to the nebulizer 2. Both waveforms have a period p of 7.8 µS giving them a frequency of 1/7.8 µS which is approximately 128 KHz. In both cases the waveforms are chopped (stopped/OFF) for a period of time x. In this case the off time x is equal to the on time x. The aerosol generator may be operated in this mode to achieve 50% aerosol output.

Figure 30:
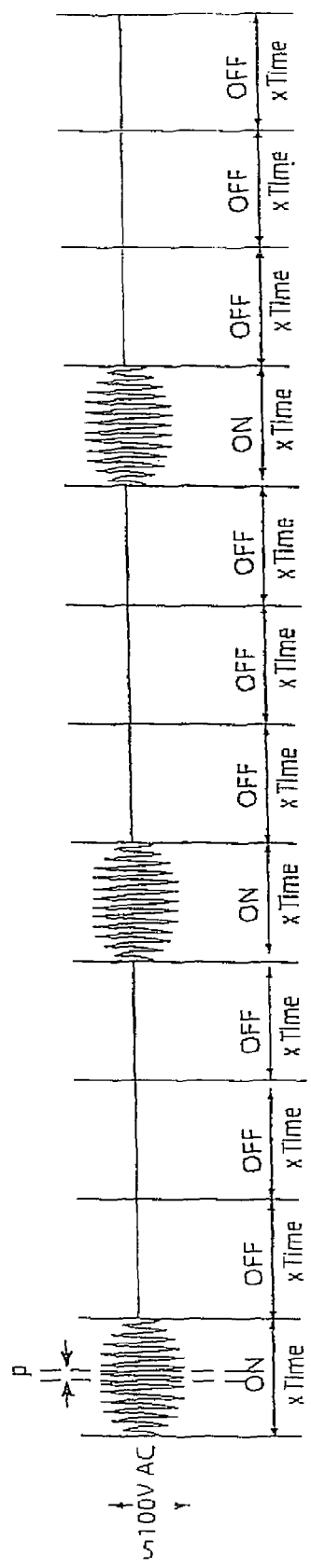
FIGS. 30 and 31 are graphs of DC voltage versus time and AC voltage versus time respectively to achieve a 25% aerosol output
Figure 31:
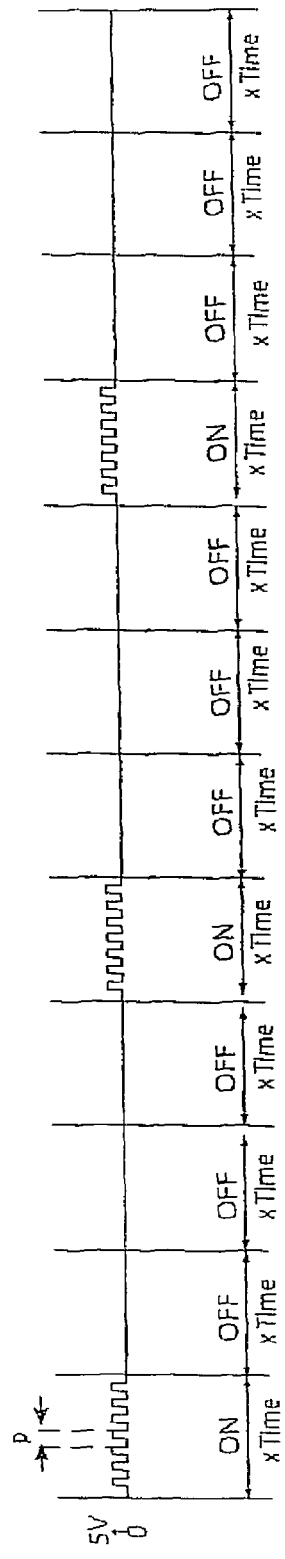

In another exemplary case, referring to FIG. 30 there is illustrated a 5V DC square waveform output from microprocessor 4 to drive circuit 6. FIG. 31 shows a low power, ~100V AC sine waveform output from the drive circuit 6 to the nebulizer 2. Both waveforms have a period p of 7.8 µS giving them a frequency of 1/7.8 µS which is approximately 128 KHz. In both cases the waveforms are chopped (stopped/OFF) for a period of time x. In this case the off time is 3x while the on time is x. The aerosol generator may be operated in this mode to achieve 25% aerosol output.

Figure 32:
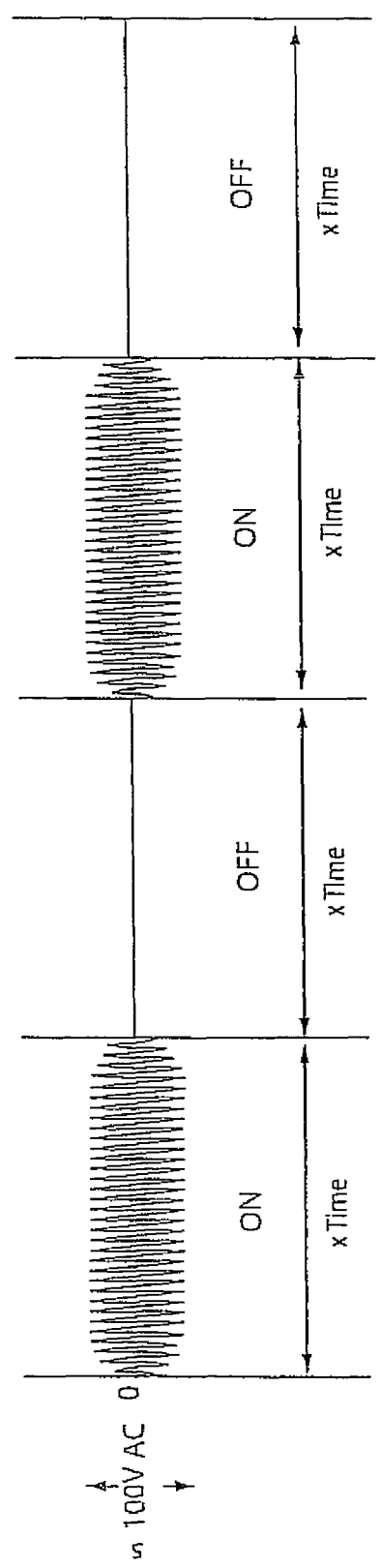
FIG. 32 is a graph of AC voltage versus time; and illustrates an output waveform from a drive circuit to a nebulizer.

Referring to FIG. 32, in an exemplary application pulsing is achieved by specifying an on-time and off-time for the vibration of the aperture plate. If the on-time is set to 200 vibrations and off-time is set to 200 vibrations, the pulse rate is 50% (½ on ½ off). This means that the flow rate is half of that of a fully driven aperture plate. Any number of vibrations can be specified but to achieve a linear relationship between flow rate and pulse rate a minimum number of on-time vibrations is specified since it takes a finite amount of time for the aperture plate to reach its maximum amplitude of vibrations.

The drive frequency can be started and stopped as required by the microprocessor; this allows control of flow rate by driving the nebulizer for any required pulse rate. The microprocessor can control the on and off times with an accuracy of microseconds.

A nebulizer can be calibrated at a certain pulse rate by measuring how long it takes to deliver a known quantity of solution. There is a linear relationship between the pulse rate and that nebulizer's flow rate. This allows accurate control of the rate of delivery of the aerosolized aqueous solution. The ability to calibrate each nebulizer ensures that any inherent variation in output rate between each nebulizer can be eliminated. The output from each nebulizer when in-line in the insufflator circuit will be equivalent to a second nebulizer although the inherent flow rates of the two nebulizers are different. For example, to achieve a standard output of 0.044 ml/min at 1 L/min from two nebulizers, one with an inherent output of 0.088 ml/min and a second with an inherent output of 0.176 ml/min, the first nebulizer is controlled with a 50:50 on:off pulse rate, with the second set to a 25:75 on-off pulse rate so that both nebulizers give a 0.044 ml/min output. This feature ensures that the nebulizers when located in the insufflation circuit have the potential to provide exactly the same rate of aerosol output as each other. This is possible because the amount of humidity a gas can hold is a known constant dependent on controllable factors.

The pulse rate may be lowered so that the velocity of the emerging aerosol is much reduced so that impaction rain-out is reduced.

Detection of when the aperture plate is dry can be achieved by using the fact that a dry aperture plate has a well defined resonant frequency. If the drive frequency is swept from 120 kHz to 145 kHz and the current is measured then if a minimum current is detected less than a set value, the aperture plate must have gone dry. A wet aperture plate has no resonant frequency. The apparatus of the present invention may be configured to determine whether there is any of the first fluid in contact with the aerosol generator 2. By determining an electrical characteristic of the aerosol generator 2, for example the current flowing through the aerosol generator 2, over a range of vibration frequencies, and comparing this electrical characteristic against a pre-defined set of data, it is possible to determine whether the aerosol generator 2 has any solution in contact with the aerosol generator 2. FIG. 33 illustrates a curve 80 of frequency versus current when there is some of the solution in contact with the aerosol generator 2, and illustrates a curve 90 of frequency versus current when there is none of the solution in contact with the aerosol generator 2. FIG. 33 illustrates the wet aperture plate curve 80 and the dry aperture plate curve 90.

Humidity may be generated via the aerosolization of any aqueous solution. Relative humidity in the 50-100% range would be optimum. The control module can generate a nebulizer output of any defined relative humidity percentage based on the insufflator flow. These solutions include any aqueous drug solution. Solutions with salt concentrations in the range 1 µM-154 mM would be optimum.

The use of the nebulizer to humidify the insufflation gas prior to entering the body will eliminate the need for the body to humidify the gas once it is inside the body, thereby minimizing body heat loss by internal evaporation.

The control in nebulizer output allows proportional delivery of the required amount of humidity according to the amount of insufflation gas entering the body. In addition, this control of aerosolization rate will prevent overloading of the insufflation gas with aerosol, which would obscure the surgeons view.

Exemplary embodiments of the present invention provide a system that can deliver different flow rates at different stages of the surgical procedure. Examples of such different flow rates include:
 (i) delivering at 100% at the start of the procedure (Bolus);
 (ii) delivering at a much lower rate say 5% during the procedure itself (Lower flow rate avoid fogging);
 (iii) delivering at 100% at the end of the procedure (Bolus);
 (iv) any combination of the above sequencing with variable % values.

In an exemplary case, the controller which controls the operation of the aerosol generator is pre-set to deliver a set amount of aerosol into the insufflation gas. For example, the controller may be set to deliver an amount of 5% into a flow of 1 liter per minute of insufflation gas to avoid fogging. The controller may be pre-set in the factory to operate in this manner. Alternatively, there may be a user interface such as a switch, or keypad which may be used to change the setting. In these arrangements, control responsive to an insufflation gas flow sensor is not essential.

In addition to acting as a humidifying agent, the nebulizer may also act to deliver any agent presented in an aqueous drug solution. The system may facilitate delivery of, for example, pain-relief medications, anti-infectives, anti-inflammatory, and/or chemotherapy agents in aerosol form to the body cavity. These therapeutic agents may also act as humidifying substances in their own right.

The nebulized liquid entrained in the insufflation gas may contain any desired therapeutic and/or prophylactic agent. Such an agent may for example be one or more of an analgesic, an anti-inflammatory, an anaesthetic, an anti-infective such as an antibiotic, an anti-cancer chemotherapy agent, and/or any agent which interferes with processes that result in the adhesion function.

Typical local anaesthetics are, for example, Ropivacaine, Bupivacaine, and Lidocaine.

Typical anti-infectives include: antibiotics such as an aminoglycoside, a tetracycline, a fluoroquinolone; and anti-microbials such as a cephalosporin; and anti-fungals.

Anti-inflammatories may be of the steroidal or non-steroidal type.

Anti-cancer chemotherapy agents may be alkylating agents, antimetabolites anthracyclines, plant alkaloids, topoisomerase inhibitors, nitrosoureas, mitotic inhibitors, monoclonal antibodies, tyrosine kinase inhibitors, hormone therapies including corticosteroids, cancer vaccines, anti-estrogens, aromatase inhibitors, anti-androgens, anti-angiogenic agents, and other antitumour agents.

The agent which interferes with the adhesion function may be any of those outlined in PCT Application Publication No. WO2005/092264A, the entire contents of which are incorporated herein by reference. In particular, the agent may be a crystalloid, hyaluronic acid, polyethyleneglycol, Tranilast (N-($3^1,4^1$-dimethoxycinnamoyl) anthranilic acid) or a Neurokinin 1 receptor (NK-1R) agonist, such as Aprepitant.

Typical analgesics include aspirin, acetaminophen, ibuprofen, naproxen, a Cox-2 inhibitor such as celecoxib, morphine, oxycodone, and hydrocodone.

To aid drug delivery at least some of the surfaces which come into contact with the drug may be coated. Any suitable coating may be used such as those with hydrophobic properties will cause the drug to repel from the surface and assist in maintaining the aerosol in motion through to the patient. PTFE based coatings such as Teflon are examples of appropriate coatings.

Alternatively or additionally, an appropriate electrostatic charge may be used to assist in maintaining the aerosol in motion. If a drug has a particular charge, adding a similar charge to a surface with which they come into contact will cause the aerosolized drug to repel from the surface, thus keeping the drug in the aerosol path to the patient.

These approaches may be applied to any aerosolized drug delivery system including but not limited to insufflation systems of the type described herein. It may be applied to nebulization/aerosolization systems in general for home and/or hospital use.

Exemplary systems of the present invention may be used for precise controlled delivery of drug and/or humidity during insufflation. No heating is required. Consequently there is no risk of damage to drugs due to heating. The system may be used to provide precise control over aerosol output, where such control may be exercised, for example, by utilizing pulse rate control. The system may be used for targeted delivery of a range of drugs, thereby reducing systemic side effects. In addition the system provides alleviation of post-surgical pain experienced by the patient.

Figure 2:
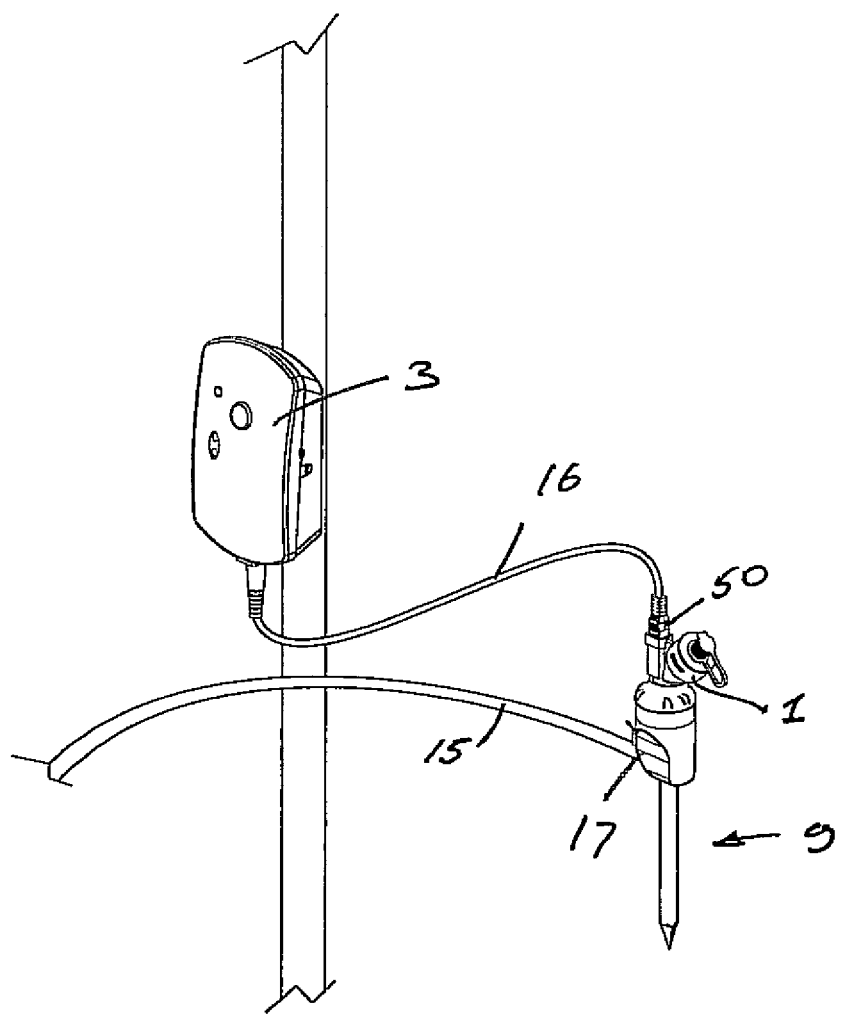
FIG. 2 is a perspective view of another apparatus in accordance with the present invention.
Figure 3:
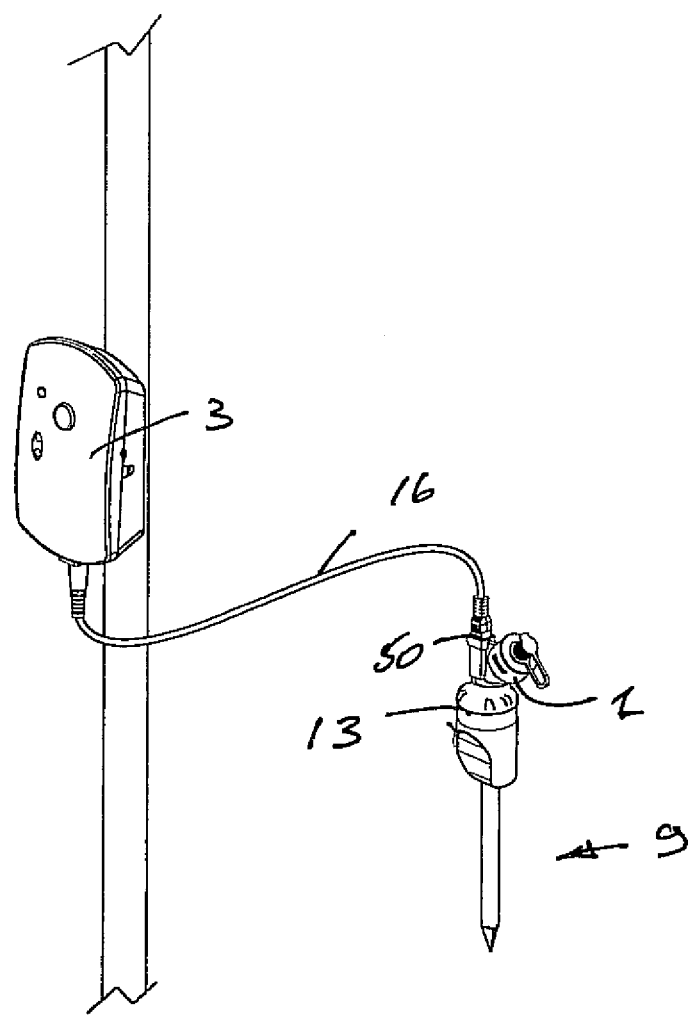
FIG. 3 is a perspective view of another apparatus in accordance with the present invention.

Referring to FIGS. 2 and 3 an aerosol generating element 2 is positioned adjacent to the patient as an attachment to the trocar tool/instrument 9 with a remote located drive controller 3, connected via a lead 16 to the aerosol generating element 2.

Figure 4:
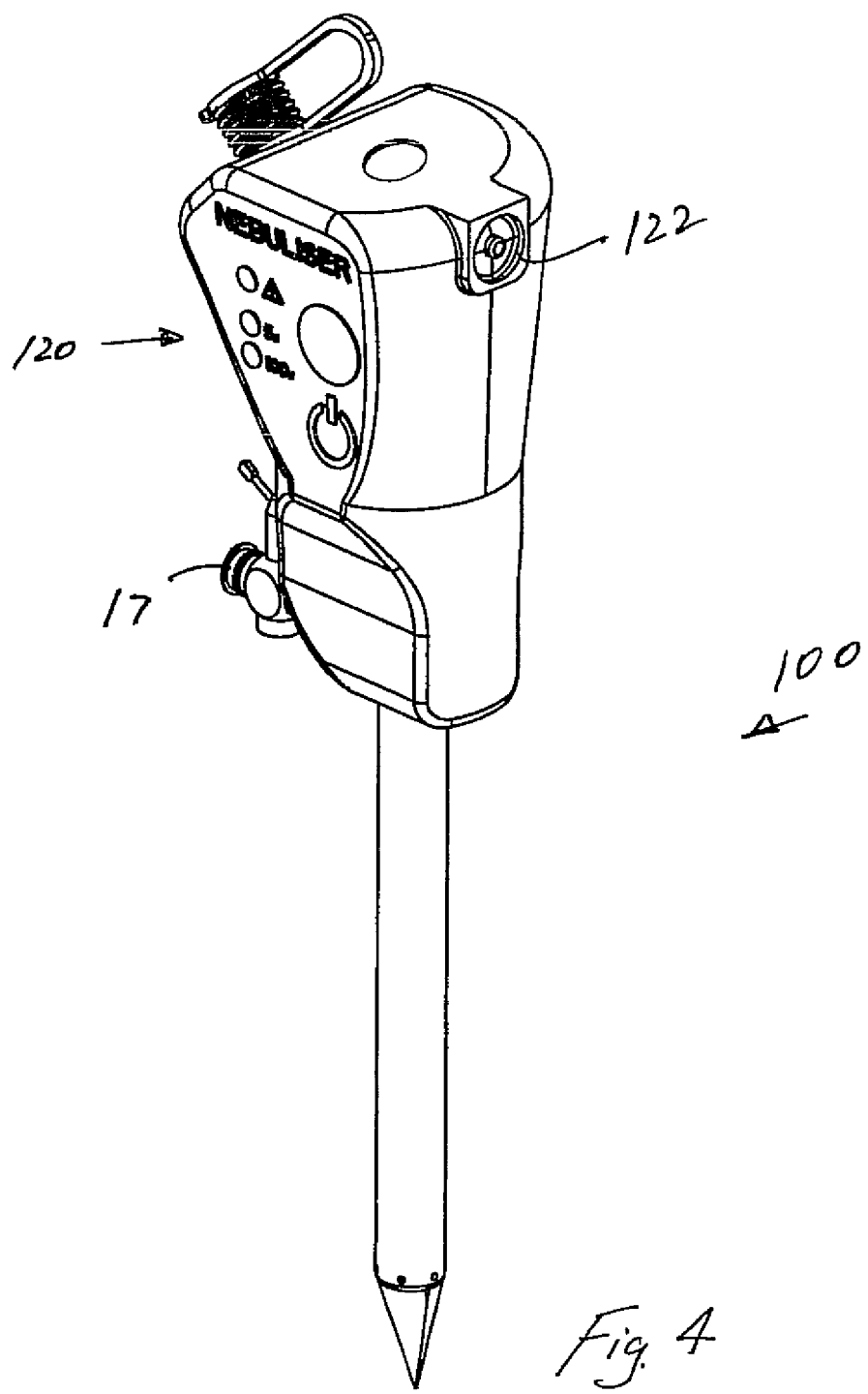
FIG. 4 is a perspective view of another apparatus in accordance with the present invention.
Figure 5:
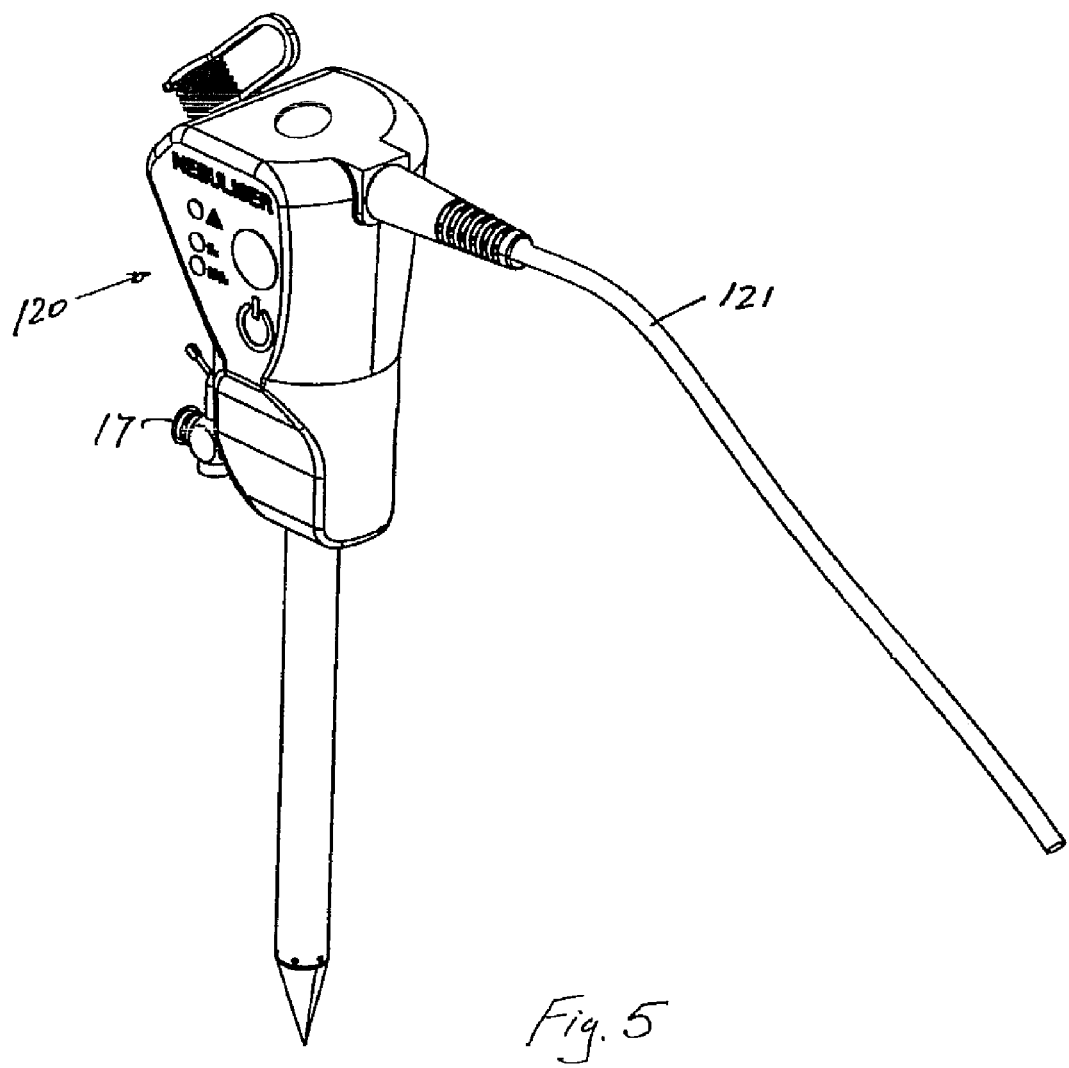
FIG. 5 is a perspective view of the apparatus of FIG. 4 with a lead connected.
Figure 9:
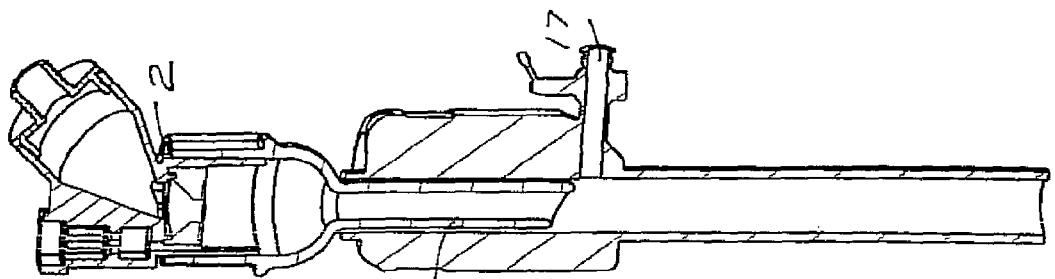
FIG. 9 is a cross sectional view of the apparatus of FIG. 8.
Figure 8:
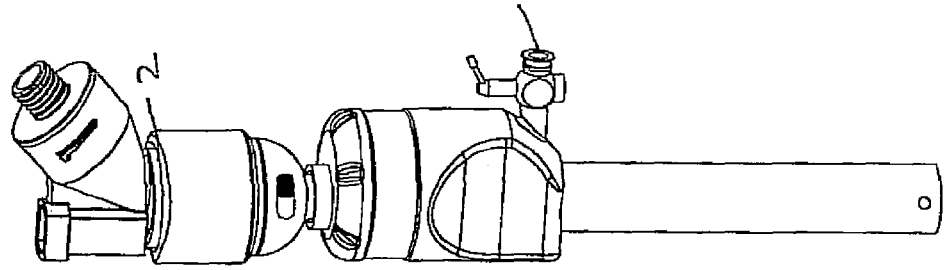
FIG. 8 is a perspective view of the apparatus of FIGS. 6 and 7 mounted to a trocar.
Figure 7:
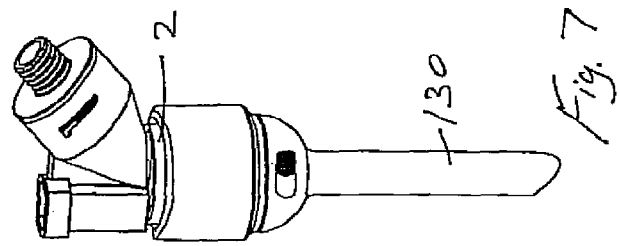
FIG. 7 is a perspective view of the apparatus of FIG. 6 assembled.
Figure 6:
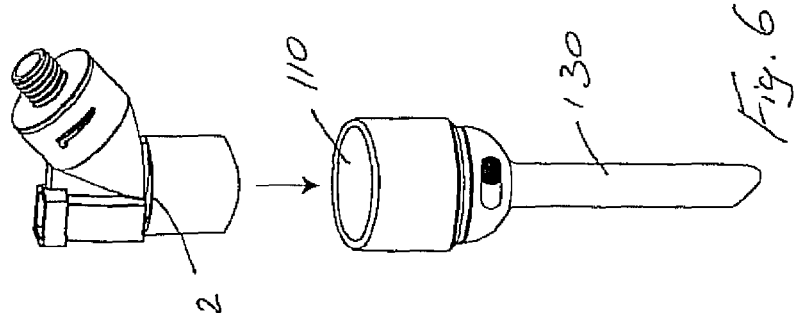
FIG. 6 is an exploded view of another apparatus in accordance with the present invention.

Referring to FIGS. 4 and 5, in another arrangement the aerosol generating element is integrated into a trocar tool/instrument 100 and the controller for the aerosol generator is also fully integrated into the trocar.

Referring to FIGS. 6 to 9, the aerosol generating device 2 may be inserted into an entry port 110 of a surgery trocar 111. The trocar 111 may be a conventional trocar with an entry port having a diameter of circa 10 mm. Such trocars are typically one used for a camera. A size of about 10 mm facilitates maximum inflow of aerosol.

The delivery of the aerosolized medicament can occur at the start of the procedure and be delivered in bolus. At the start of the procedure, the peritoneum is being inflated by means of the flow of insufflator gas. This gas flow will help to entrain the aerosolized medicament to the pneumoperitoneum regions. The surgeon can temporarily remove the camera from the trocar port to facilitate insertion and positioning of the aerosolizing unit.

The medicament can also be aerosolized when the peritoneum is inflated, by assisting the flow of aerosol by generating a larger pressure drop across the peritoneum cavity. This can be accomplished by creating an artificial leak or vent of CO2 from the cavity. This could be designed into the spigot of the aersolising device that fits into the trocar port 110.

The aerosol may be generated directly above the trocar entry point into the pneumoperitoneum and in one embodiment can be powered via a cable 16 attached to the separate controller unit 3. In an exemplary case illustrated in FIG. 2, the insufflator gas from the insufflator 12 enters the trocar 9 from the line 15 via a separate port 17 and generated aerosol is carried into the pneumoperitoneum by entrainment in the gas flow and through the effects of gravity and diffusion. The controller 3 may be located near to the trocar location or at some remote location as allowed by the cable length 16 and the surgeon's desired ergonomical preferences.

In another exemplary case illustrated in FIG. 3, the trocar 9 may provide a port 13 for the aerosol generator 2 only with no provision for insufflator gas inflow. In this embodiment, the generated aerosol is carried into the pneumoperitoneum through the effects of gravity, diffusion, and the residual velocity of aerosol after exiting the aerosol generator. The controller 3 may be located near to the trocar location or at some remote location as allowed by the cable length 16.

In the device illustrated in FIGS. 4 and 5, both the aerosol generator 2 and control 3 functionality are integrated into one self contained unit and placed in the trocar housing 100. The aerosol is generated directly above the trocar entry point into the pneumoperitoneum. The insufflator gas enters the trocar via a separate port 17 and generated aerosol is carried into the pneumoperitoneum by entrainment in the gas flow and through the effects of gravity and diffusion. Control functionality is available directly at the trocar body via buttons, indicator lights, displays, or other user interfaces 120. The integrated device may be operated via internal battery power or from an external power source via a power supply cable. The device may also have a charger port 122 for charging of an internal battery via an external power supply cable 121. Therefore it is possible that there are no attached or trailing cable leads on the aerosol generating device during the surgical procedure greatly aiding the surgeon's ease of use of the equipment and contributing to the whole aesthetics of the equipment set up.

The integrated trocar may have no provision for insufflator gas inflow. The control functionality may be driven by a battery built into the trocar nebulizer body. In this embodiment, the generated aerosol is carried into the pneumoperitoneum through the effects of gravity, diffusion and the residual velocity of aerosol after exiting the aerosol generator.

The nebulizer on the trocar may be provided with a particular geometrical configuration to receive mating nebule geometry. This will facilitate the aerosolization of this drug only within the predesigned nebule and no other drug. This would allow for targeted delivery of small volumes of high concentration drug to the aperture plate, thus minimizing residual drug wastage.

Referring to FIGS. 6 to 9 an aerosol generator trocar insert 130 delivers aerosol through the trocar with no provision for insufflator gas inflow. The trocar insert 130 is of a length that will allow aerosol generated to be delivered beyond any trocar valve. In this embodiment, the generated aerosol is carried into the pneumoperitoneum through the effects of gravity, diffusion and the residual velocity of aerosol after exiting the aerosol generator. The controller 3 may be located near to the trocar location or at some remote location as allowed by the cable length.

The aerosol generator and control functionality may be integrated into the aerosol generator trocar insert. The trocar insert will be of a length that will allow aerosol generated to be delivered beyond any trocar valve. In this case the aerosol is generated directly above the trocar entry point into the pneumoperitoneum. The insufflator gas enters the trocar via a separate port 17 and generated aerosol is carried into the pneumoperitoneum by entrainment in the gas flow and through the effects of gravity and diffusion. Control functionality may be available directly at the trocar body via buttons, indicator lights, displays or other user interfaces. The integrated device may be operated via internal battery power or from an external power source via a power supply cable. The device may also have provision for charging of the internal battery via the external power supply cable.

Alternatively, the aerosol generator trocar insert may have no provision for insufflator gas inflow. In a further embodiment, the control functionality may be driven by a battery built into the trocar insert aerosol generator body. In this embodiment, the generated aerosol is carried into the pneumoperitoneum through the effects of gravity, diffusion and the residual velocity of aerosol after exiting the aerosol generator.

Figure 10:
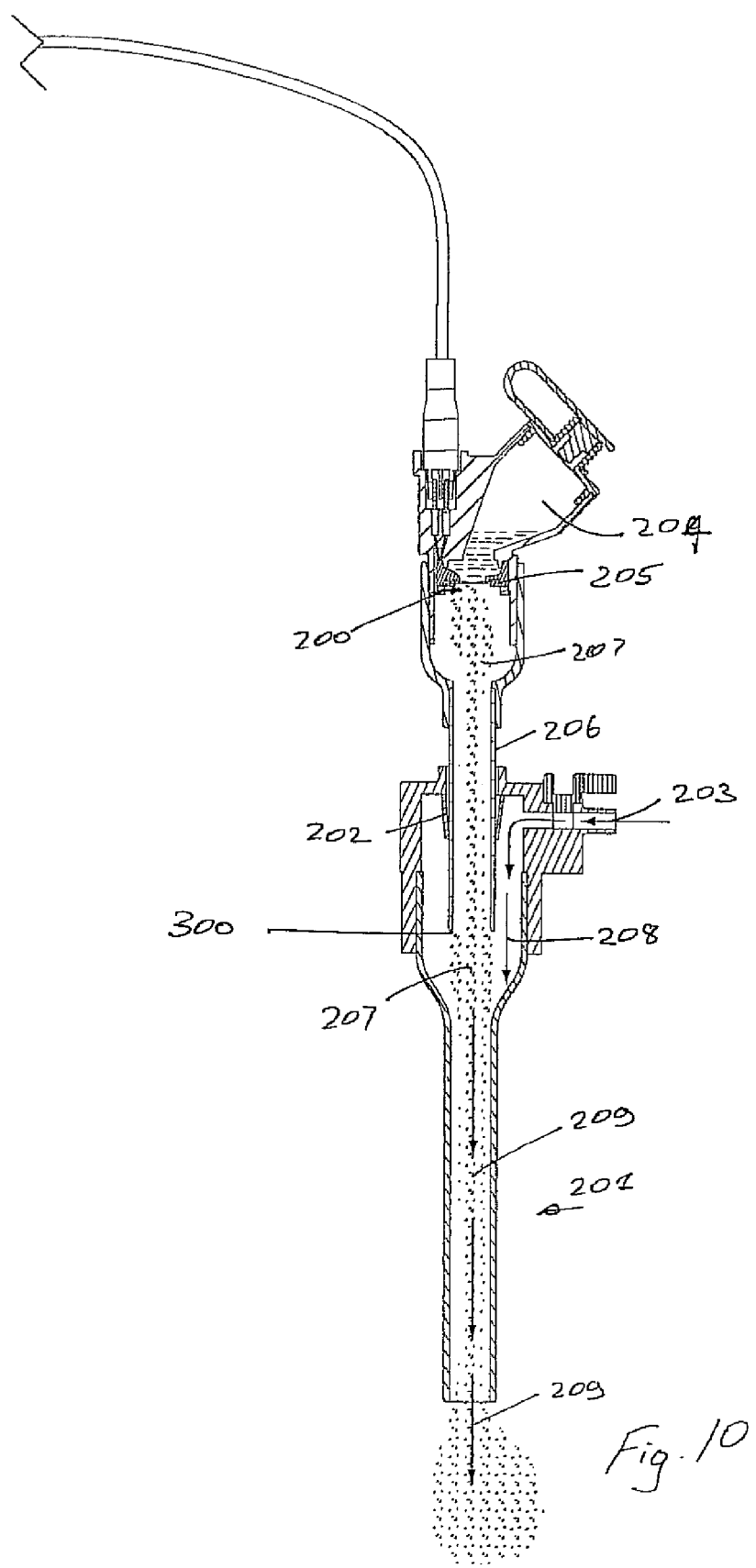
FIG. 10 is a cross sectional view of another aerosol generator system mounted to a trocar.
Figure 11:
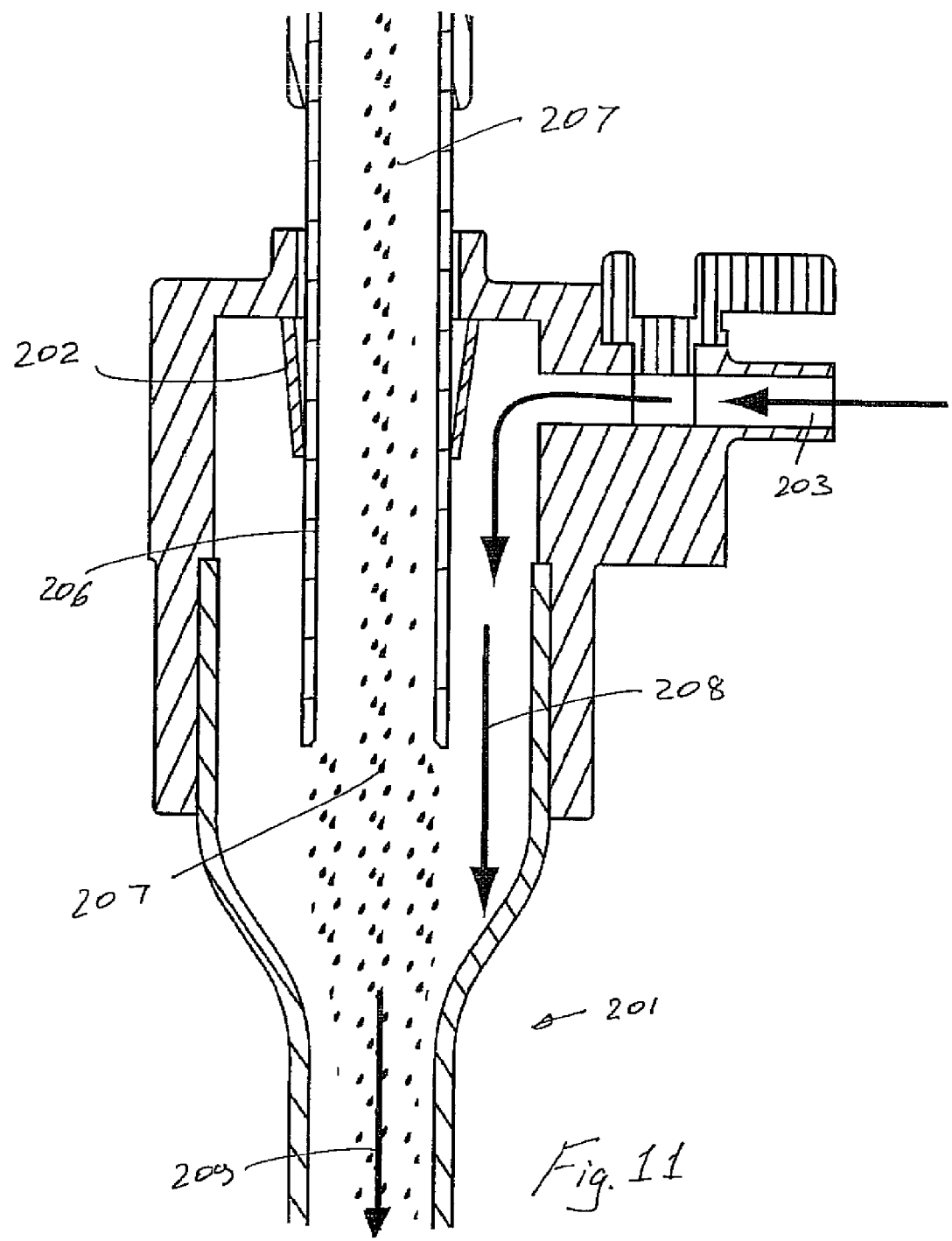
FIG. 11 is an enlarged view of part of the apparatus of FIG. 10.

Referring to FIGS. 10 and 11 there is illustrated another aerosol generator system 200 mounted to a trocar 201 having a proximal trocar seal 202. In this case the trocar 201 has an inlet 203 for insufflation gas. The aerosol generator system 200 comprises a vibrating mesh/plate 205 and a reservoir 204 for fluid to be aerosolized. Aerosol 207 passes down through a delivery tube 206 and is entrained with insufflation gas 208. The mixture 209 is then delivered through the trocar 201 into a patient's abdomen. The trocar comprises a housing having a proximal end to which the aerosol generator is mounted and a distal end through which aerosol is delivered. The trocar has a proximal entry port 203 for insufflation gas. The apparatus comprises an aerosol delivery tube means extending from the aerosol generator 200 into the trocar housing. The aerosol delivery tube has an aerosol outlet 300 which is located distally with respect to the insufflation gas entry port 203 of the trocar. In this case the aerosol outlet 300 of the aerosol delivery tube 206 extends into the trocar for a length which is at least 10%, at least 15%, or at least 20% of the length of the trocar. There is a proximal seal 202 between the trocar and the aerosol delivery tube 206.

The embodiment of FIGS. 10 and 11 has the advantage of ease of manufacture and use. It does not require auxiliary seals and does not require elaborate fluid pathways.

Figure 12:
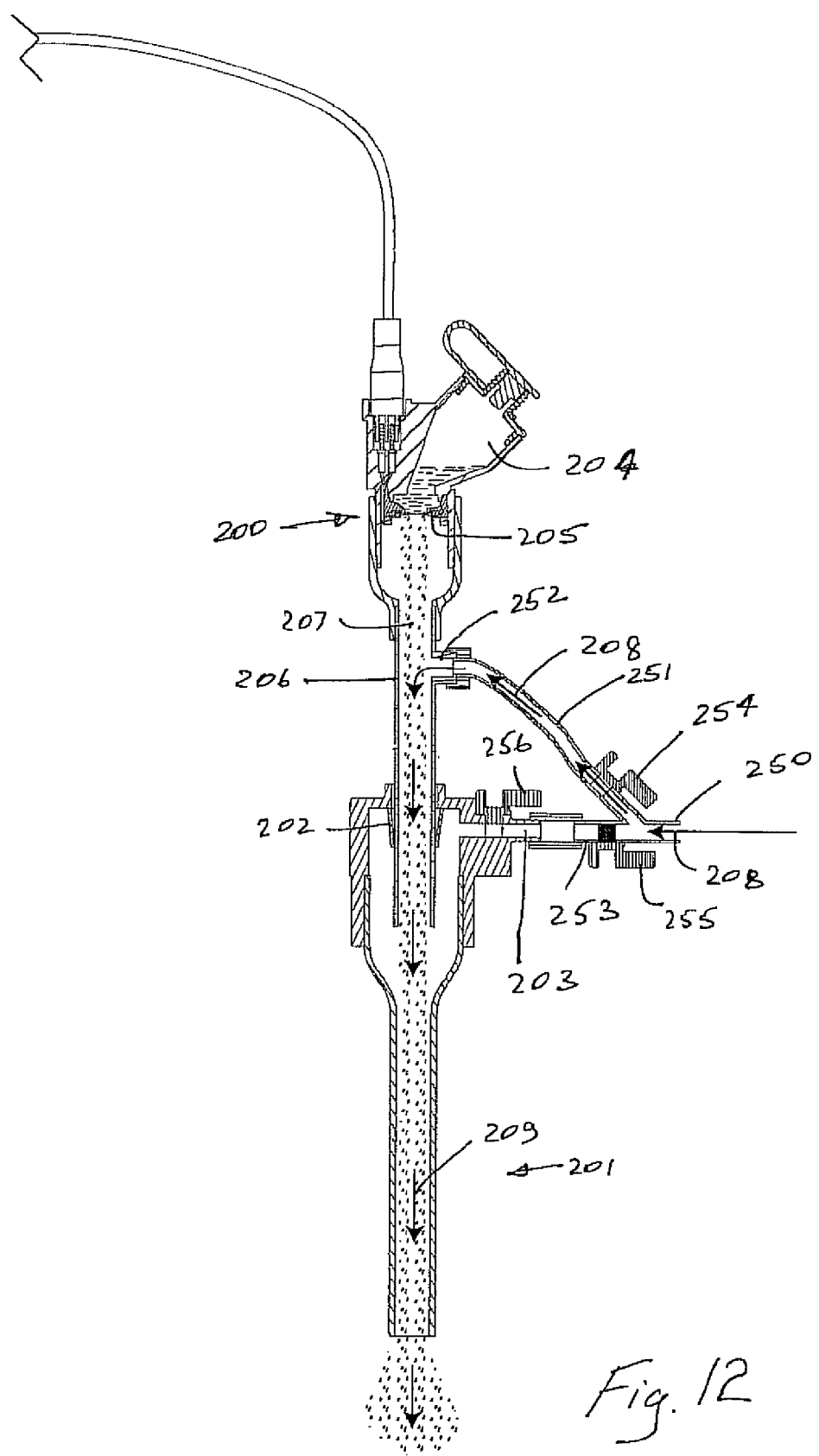
FIG. 12 is a cross sectional view of a further aerosol generator system mounted to a trocar.
Figure 13:
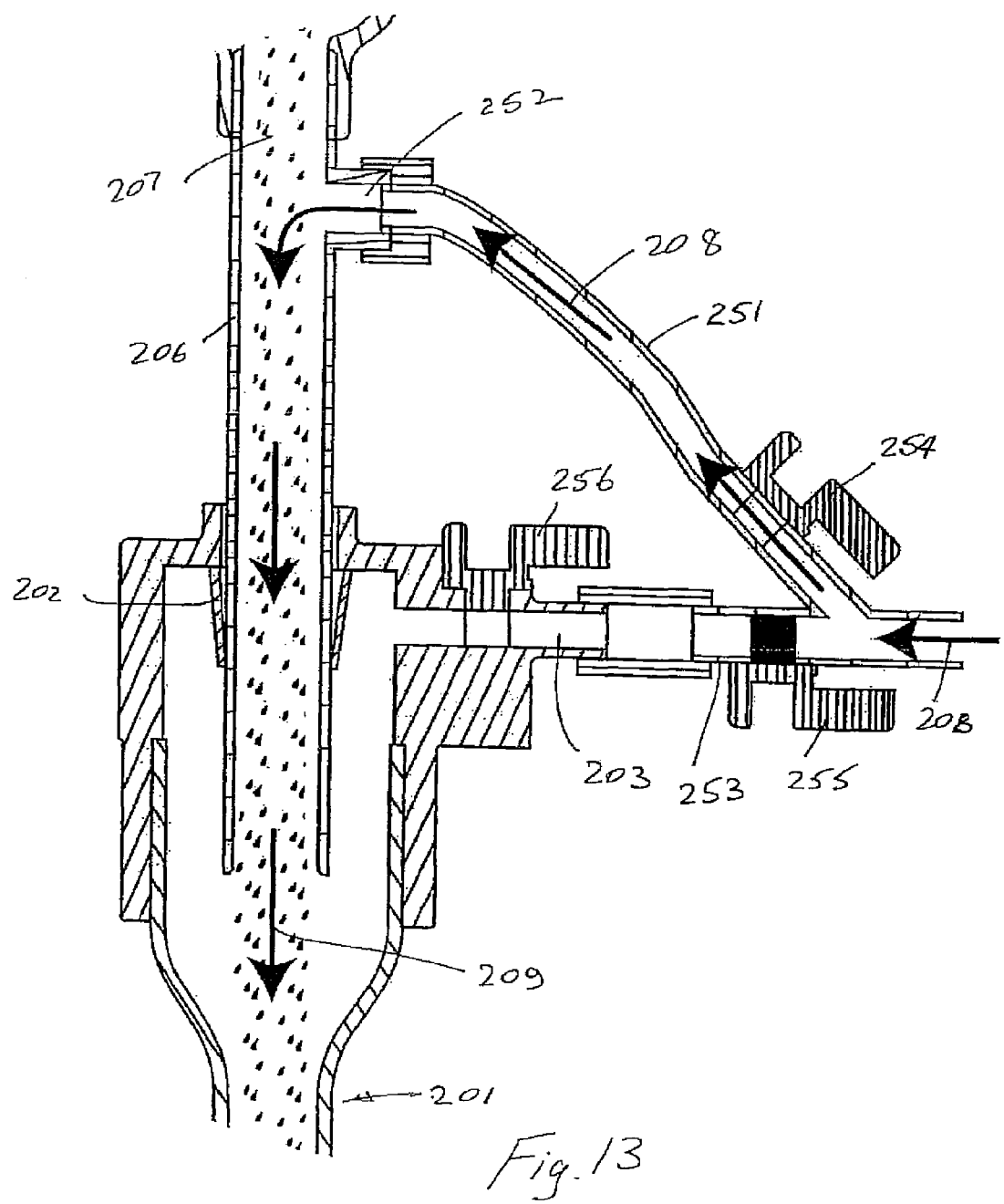
FIG. 13 is an enlarged view of part of the apparatus of FIG. 12.

Referring to FIGS. 12 and 13, there is illustrated another aerosol generator system and trocar which is similar to that described with reference to FIGS. 10 and 11 and like parts are assigned the same reference numerals. In this case an inlet supply line 250 for insufflation gas is split into a first leg 251 for delivery to an inlet 252 below the vibrating plate/mesh 205 and a second leg 253 for delivery to the trocar inlet 203. There is a valve 254 on the aerosol generator supply line 251 and valves 255, 256 on the trocar supply line 253. In use, the valve 255 is closed and the valve 254 is opened when it is desired to deliver insufflation gas to the aerosol generator. The generated aerosol 207 is entrained in the insufflation gas, and the mixture 209 is delivered through the trocar 201. The system may comprise various quick release couplings to facilitate removal of the aerosol generator 200 after completion of the aerosol delivery. For decoupling, the valve 254 is closed and the valves 255, 256 are opened to facilitate direct flow of insufflation gas to the trocar inlet port 203. On release of the coupling, the aerosol generator 200 can be removed, allowing the continuing function of the trocar 201, for example for vison/camera systems. In this version the aerosol delivery tube comprises an entry port for receiving a flow of insufflation gas. In this case the apparatus comprises flow diverting means for delivery of insufflation gas to the insufflation gas entry port of the trocar 203 and/or to the insufflation gas entry port 252 of the aerosol delivery tube 206. This system conveys the CO2 gas and thus entrains the aerosol with improved flow rate to the distal end of the trocar.

Figure 14:
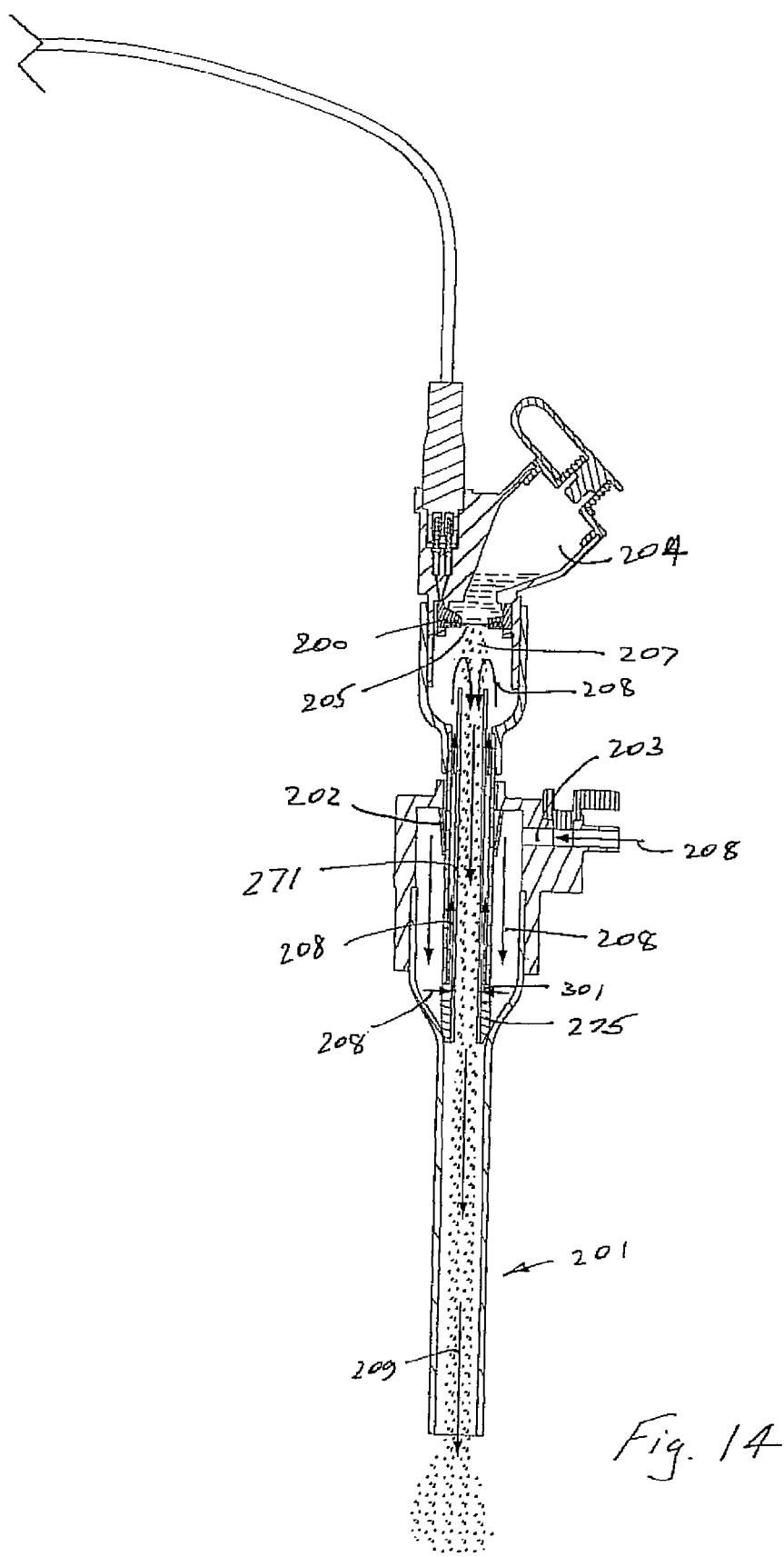
FIG. 14 is a cross sectional view of another aerosol generator system mounted to a trocar.
Figures 15, 17:
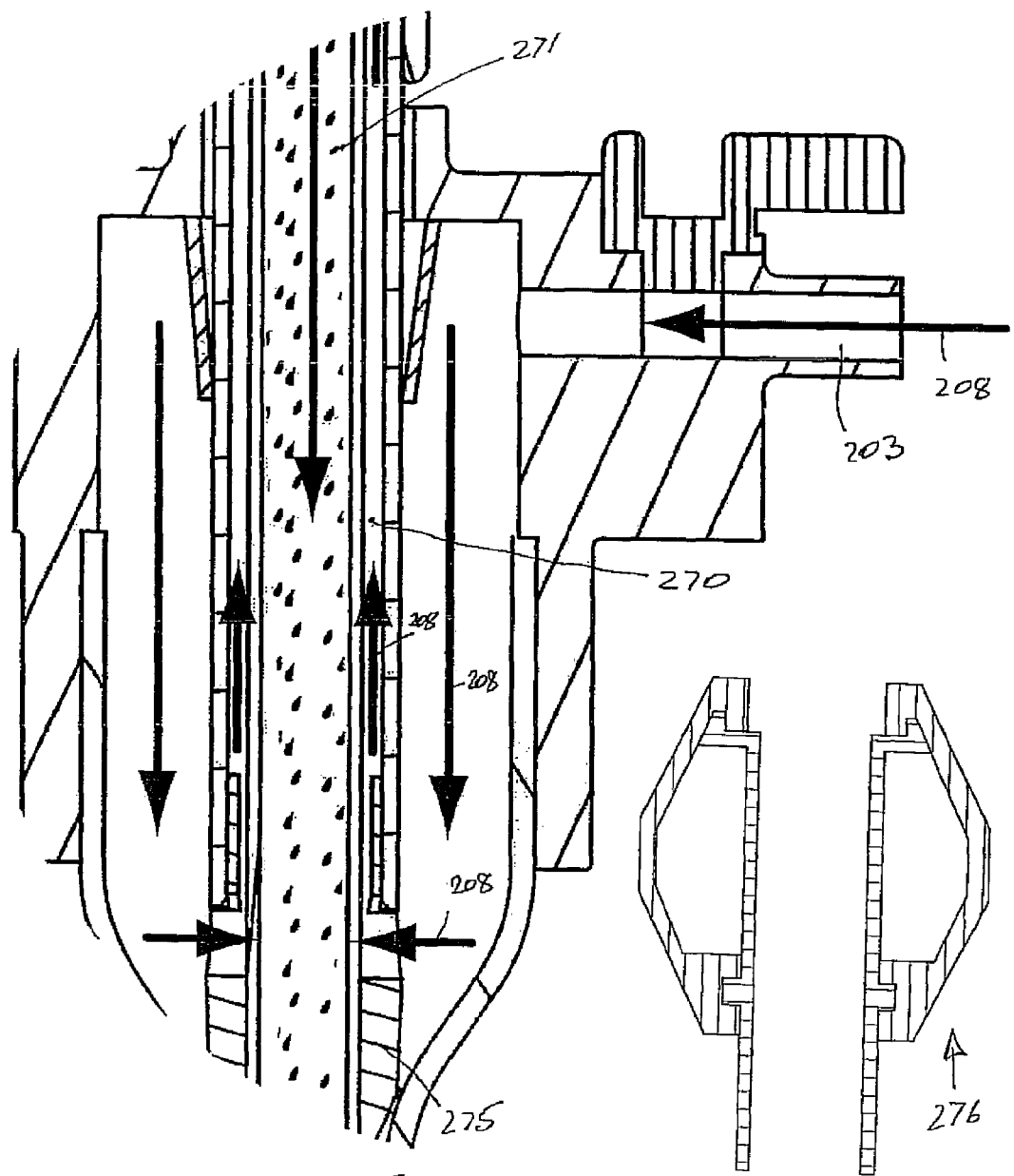
FIG. 15 is an enlarged view of one part of the apparatus of FIG. 14.
FIG. 17 is a cross sectional view of an alternative seal.
Figure 16:
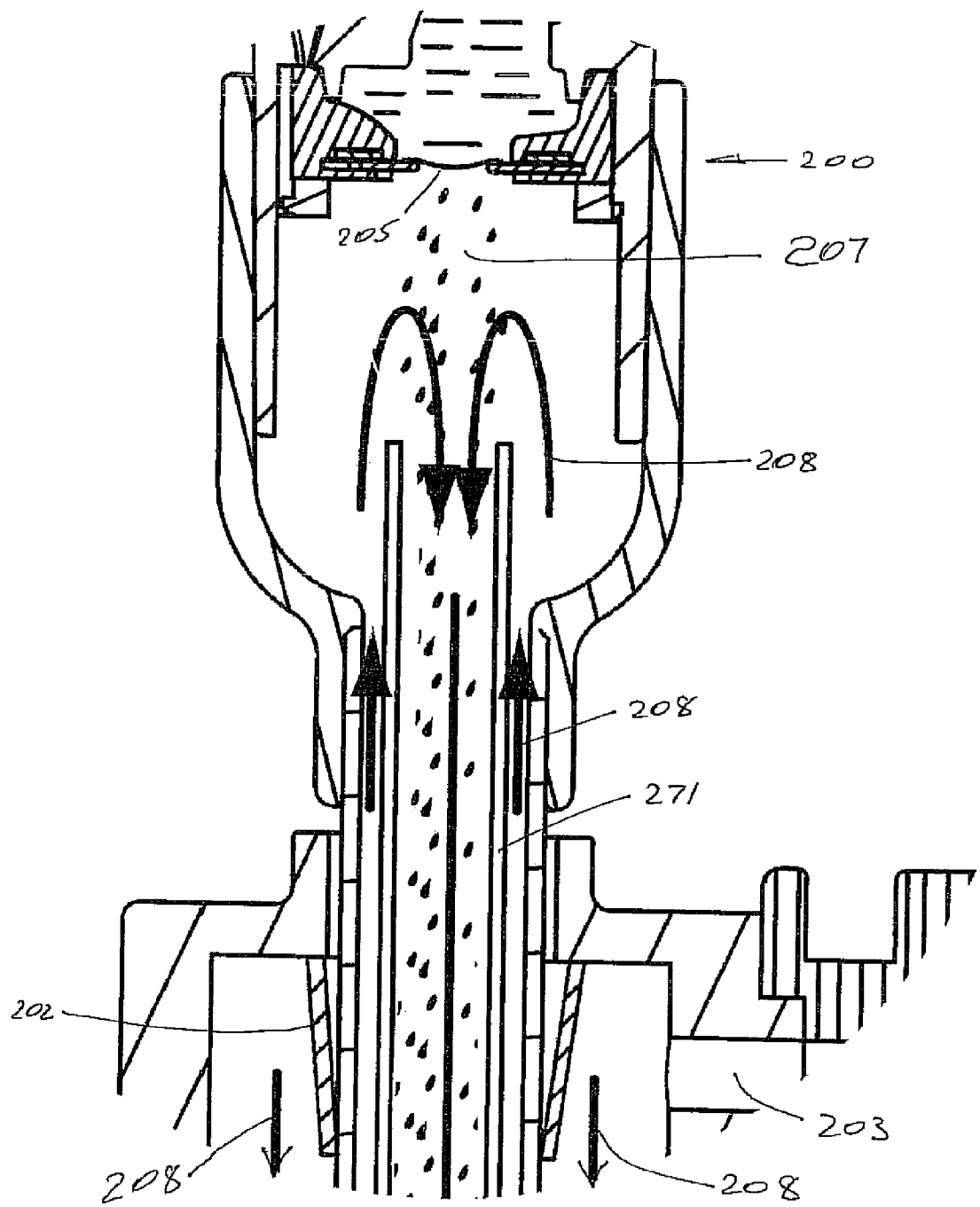
FIG. 16 is an enlarged view of another part of the apparatus of FIG. 14.

As illustrated in FIGS. 14 to 17, another exemplary embodiment again comprises an aerosol generator 200 and a trocar 201. Parts similar to those described in other embodiments are assigned the same reference numerals. In this case insufflation gas is directed along a pathway comprising a first upwardly directed leg 270 to the aerosol generator 205 at which the generated aerosol is entrained in the insufflation gas and the mixture 209 is delivered along a downwardly directed leg 271 to the trocar 201. There is a seal 275 to the trocar body to ensure that the insufflation gas passes up through the leg 271. The seal 275 may be a tapered seal as illustrated in FIGS. 14 and 15. Alternatively, a seal 276 (FIG. 16) of an elastometric material may be used. The seal 276 is compliant and may be used to achieve sealing with a range of tubes with different diameters. The leg 271 may have additional parts, to aid balanced flow. In this case the aerosol delivery tube means comprises an inner tube and an outer tube which are spaced-apart to define an insufflation gas flow path therebetween. In this case there is a distal seal 275 between the outer tube and the trocar. The apparatus comprises an aerosol delivery chamber and the insufflation gas flow path extends into the aerosol delivery chamber for entraining insufflation gas with the aerosol, the insufflation gas with entrained aerosol being delivered through the inner tube and extending from the inner tube into the trocar at the distal end of the tube means. In this case the distal end of the outer tube is located proximally with respect to the distal end of the inner tube to define an entry port 301 for insufflation gas.

This embodiment has an auxiliary seal and has bi-directional, co-axial fluid paths which has the advantage of eliminating the need for the additional CO2 feed line of the embodiment of FIG. 12. This eliminates additional operational steps for clinicians. It also has the advantages that it works with existing set up and devices. It entrains the aerosol closer to the delivery at the aperture plate and this improves aerosol delivery and efficiency to the patient. The aerosol delivery is more controllable using this system.

Figure 18:
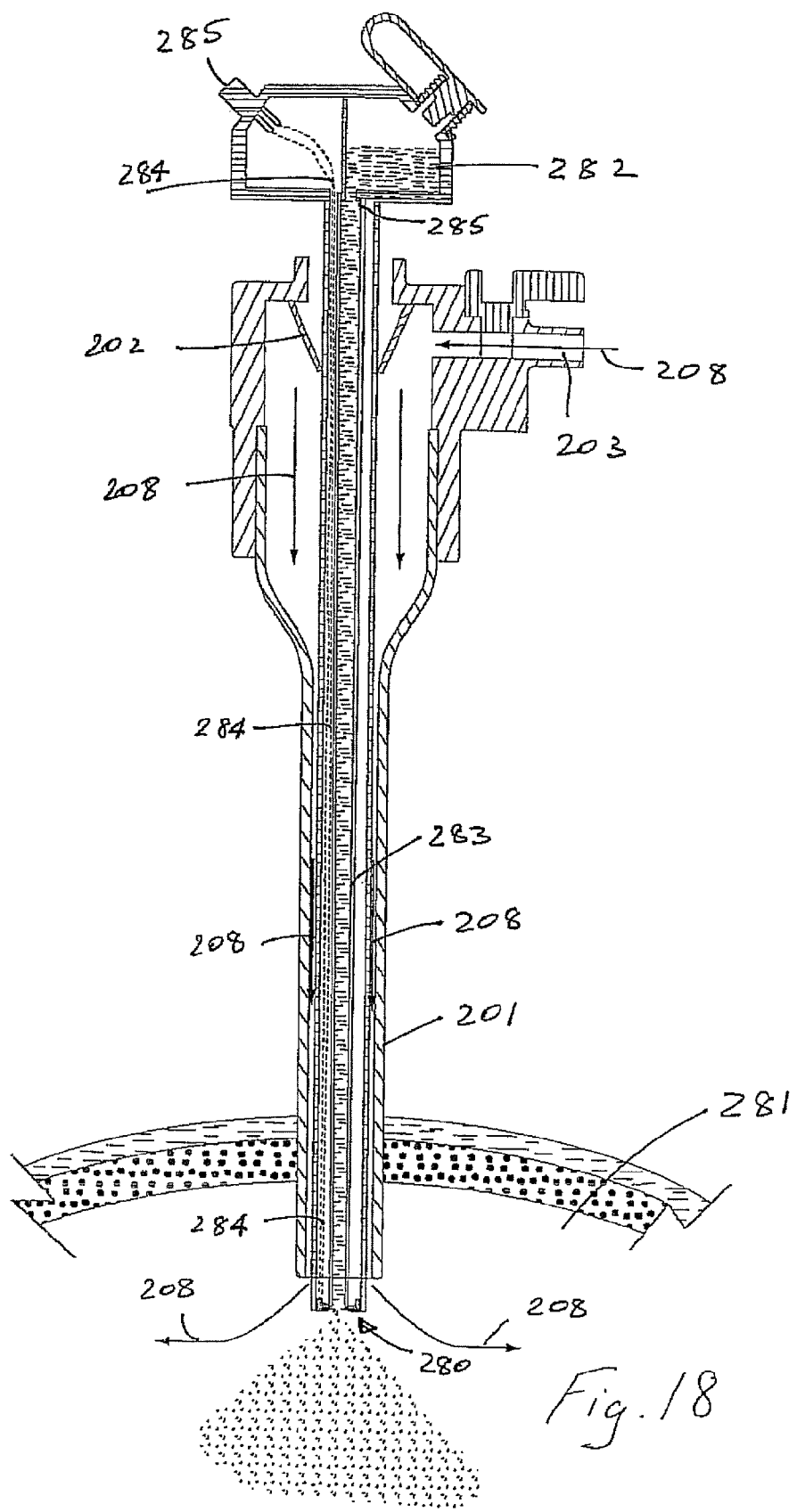
FIG. 18 is a cross sectional view of a further aerosol generator system mounted to a trocar.
Figure 19:
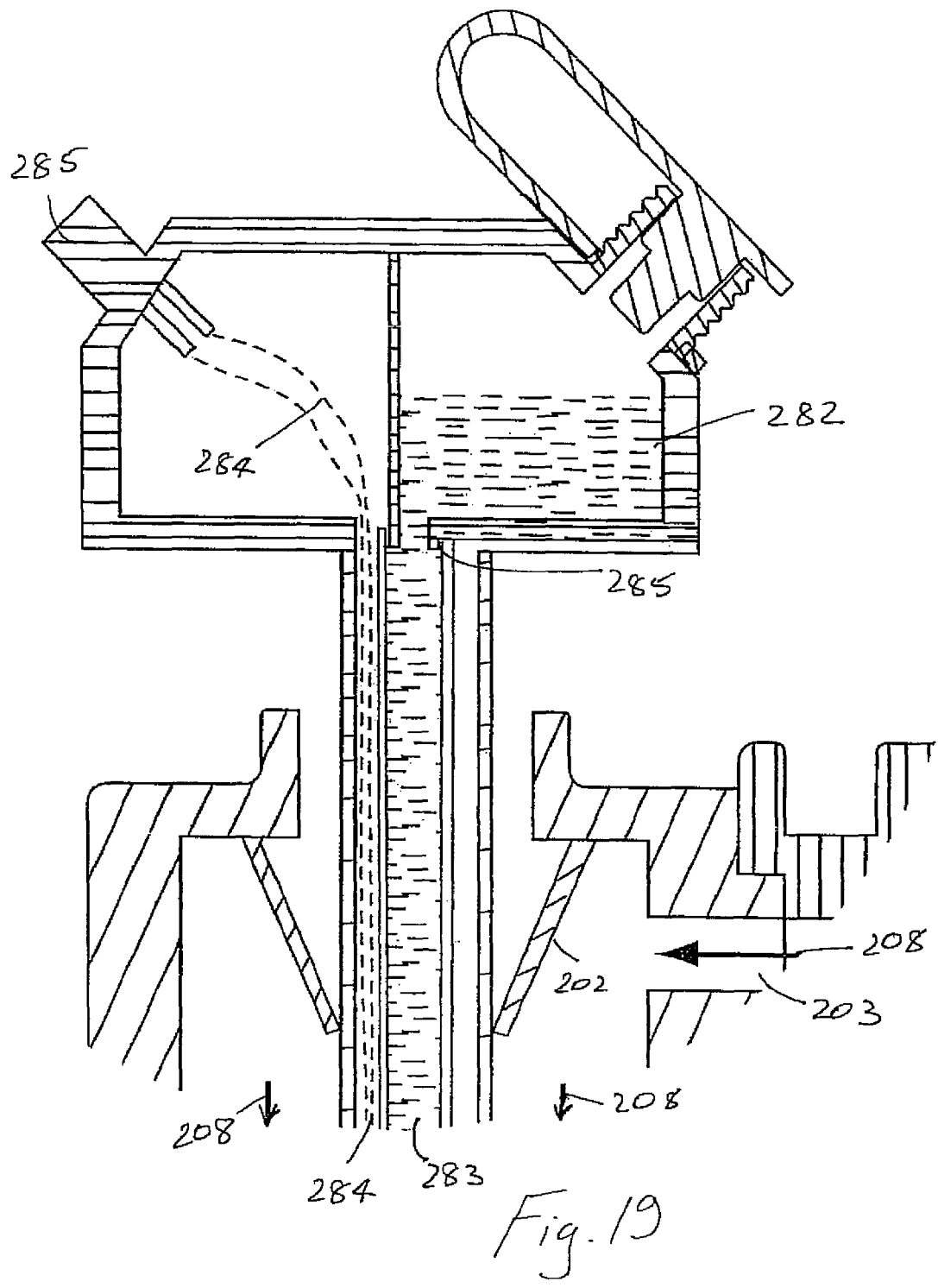
FIG. 19 is an enlarged view of one part of the apparatus of FIG. 18.
Figure 20:
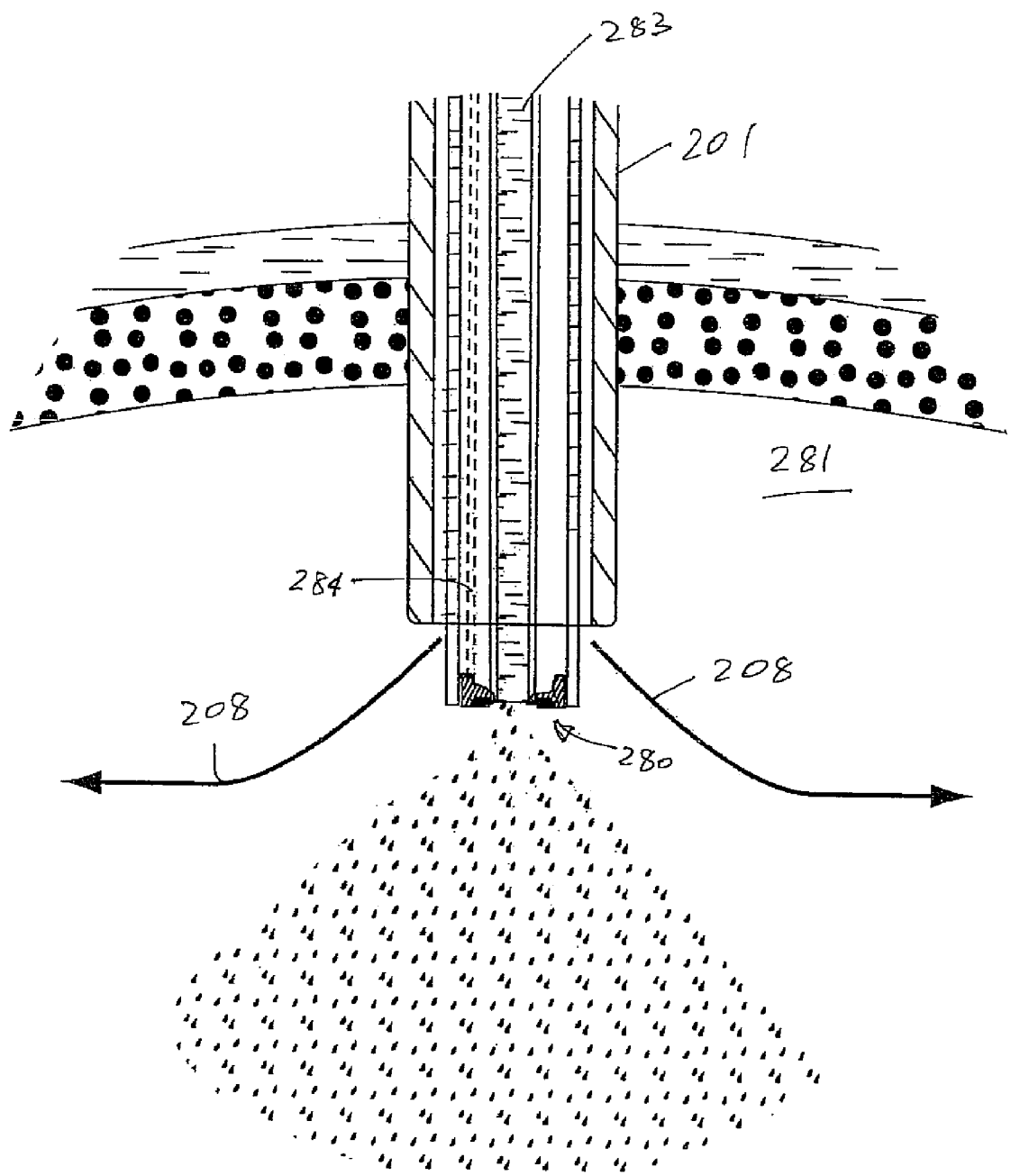
FIG. 20 is an enlarged view of another part of the apparatus of FIG. 18.

Referring now to FIGS. 18 to 20 there is illustrated another aerosol generator system 200 and associated trocar 201. Parts similar to those described in other embodiments are assigned the same reference numerals. In this case an aerosol generator vibrating plate/mesh 280 is located at the distal end of the trocar for localized generation of aerosol in or adjacent to a patient such as the abdomen 281. There is a proximal reservoir 282 for fluid to be aerosolized which is delivered to the generator 280 along a feed tube 283. The aerosol generator 280 is operated/controlled by delivering signals along a lead 284 which extends from a proximal connection part 285 to the aerosol generator 280. In use, insufflation gas passes through the trocar as illustrated and aerosol is entranced in the insufflation gas at the distal end of the trocar 201. In this case the aerosol generator is located at a distal end of the trocar. The apparatus comprises first delivery means for delivering insufflation gas to a location adjacent to the aerosol generator 280. The apparatus also comprises second delivery means for delivery of liquid to be aerosolized to the aerosol generator 280. The second delivery means in this case comprises a delivery tube extending from a housing 282 for a liquid to the aerosol generator. In this embodiment the aerosol generator is mounted to an outer tube which extends through the trocar from the liquid housing. A distal end of the outer tube is located adjacent to a distal end of the trocar. This system minimizes rain out and thus there is little or no medication loss between the aerosol generator and the patient.

The aerosol generator trocar insert may incorporate a closed cup configuration containing medication. This will facilitate the aerosolization of this drug only within the closed cup configuration and no other drug. Therefore the aerosolizing device can be used to target a particular medical condition as dictated by the drug nebule that will match the aersolising device. By positioning the aerosolizing device at the trocar the amount of the drug deposited in the pneumoperitoneum, is greatly increased by as much as two or three fold. This has the distinct advantage of aerosolizing a reduced drug volume for the equivalent therapeutic value. In addition, less aerosolizing time will be required thus shortening surgical procedures.

In one arrangement a higher concentration variant of the drug may be aerosolized. This would allow for targeted delivery of small volumes of high concentration drug to the aperture plate.

This has the distinct advantage of aerosolizing a smaller quantity of a higher drug concentration which would have the equivalent therapeutic value of a larger quantity of standard drug concentration. In this way, the delivery time is substantially shortened. Therefore the aerosolizing device occupies less time in the trocar position, leading to shorter surgical procedures.

Larger particle size in the range of 5-10 microns may be aerosolized. This will further shorten delivery time and require the aersolising device to occupy less time in the trocar position These approaches enable the delivery of a complete dose and all fogging cleared during the insufflation phase in preparation for the start of the actual laparoscopic procedure.

Aerosol is generated directly at the trocar entry point to the pneumoperitoneum. This reduces rainout and loss of suspended aerosol delivered to the pneumoperitoneum due to long tubing flow lengths, constrictions and changes in flow direction. The volume of medication that is delivered as suspended aerosol to the pneumoperitoneum is increased for any given time.

Aerosol can be generated and delivered to the pneumoperitoneum completely independently of insufflator flow allowing more flexibility in the timing of aerosol delivery during the procedure.

Access to the control mechanism for the aerosol generator is nearer to the patient and accessible to the surgeon during the procedure. This reduces inconvenience and patient risk where the surgeon needs to make immediate changes in aerosol delivery during the course of a procedure.

Integration of the controller functionality into a single device removes the cable link, as the product could be battery powered. Such cables cause inconvenience to the surgeon.

Designing the trocar nebulizer to receive a prefilled nebule of a particular engagement geometry, ensures that no other drugs can be used in an 'off label' manner.

The insertion of the nebule activates the vibration mesh thus creating aerosolization, consequently pouring in a drug will not activate the vibration system to cause aerosolization.

In accordance with exemplary embodiments of the present invention, there is increased treatment effectiveness and reduced treatment time through increased proportion of medication delivered as suspended aerosol. Aerosol delivery can be activated independently of insufflator gas flow. There is increased control and accessibility to the aerosol generator for surgeon at the patient site.

There is also reduced complexity of the device and risk of inconvenience or obstruction for fully integrated aerosol generating device.

The aerosol generator trocar insert is compatible with a standard 10 mm trocar by utilizing the camera or any other suitable port.

The aerosol generator trocar insert may be removed post delivery allowing the surgeon to use to port as standard.

The aerosol generator trocar insert may be fully disposable, intended for single patient use.

The aerosol generator trocar insert may be a closed cup configuration containing appropriate medication quantity preventing excess medication delivery. There is a reduced risk of misuse of system through the use of unapproved drugs.

Using a trocar to deliver an aerosol into a cavity during procedures involving insufflation allows the concentrated local delivery of aerosol into the cavity. The aerosol can be delivered quickly with optimised flow rate, particle size and drug concentration. The dose delivered can be maximized. The aerosol generator is only required to be in situ in the trocar for a short time which means that the trocar can be used for other tools such as a camera during the procedure. By using an aerosol the entire body cavity can be coated rather than a local area by instillation. Because the aerosol generator is located at the trocar optimum delivery of aerosol during insufflation pneumoperitoneum phase can be achieved.

Referring to FIG. 34, there is illustrated another exemplary insufflation system in accordance with the present invention which is similar to that described with reference to FIG. 1. In this case an aerosol jet nebulizer 300 is located in the insufflation line.

All of the trocar systems described above may be adapted to accommodate two or more aerosol generators. Such systems with more than one aerosol generator increase nebulizer output and reduce the time required to deliver a required amount of aerosol. One such system is illustrated in FIGS. 35 and 36. In this case an insufflation insert 500 for a trocar 501 has two separate aerosol generators 502, 503. The gas flowpath in this case is similar to that described above with reference to FIGS. 14 to 16. There may be any desired number of aerosol generators. For example, FIG. 37 illustrates a modified version in which there are four aerosol generators 510, 511, 512, 513.

There may be a seal 505 between the distal end of the trocar insert 500 and the wall of the trocar to prevent insufflation gas from passing between the outer wall of the insert and the inner wall of the trocar. In an exemplary case the seal comprises a bulbous region 505 at the distal end of the insert which is an interference fit in the shaft of the trocar. Such an arrangement facilitates ease of insertion and removal of the trocar insert whilst maintaining a seal when the insert is in place in the trocar.

Figure 38:
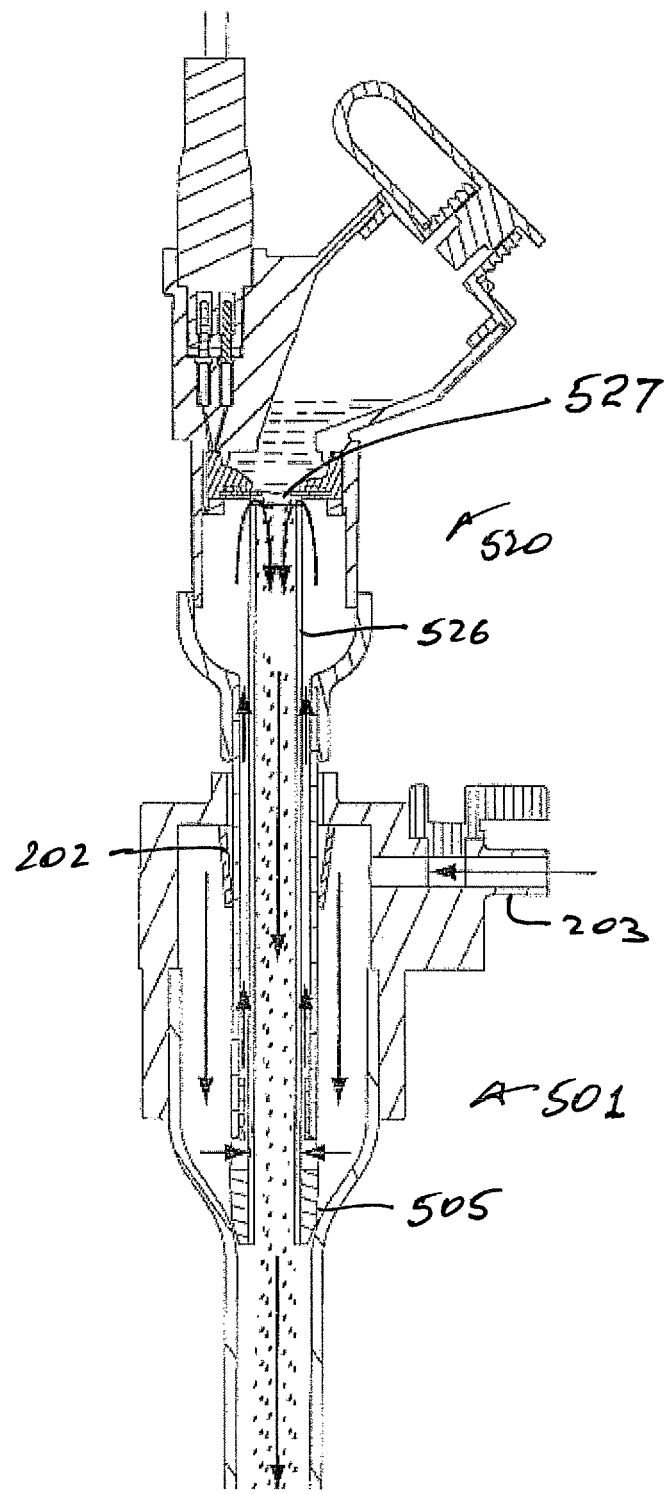
FIG. 38 is an elevational view of another apparatus in accordance with the present invention.

Referring to FIG. 38 a trocar insert 520 may have a length which is sufficient to create a seal between the trocar insert 520 and the inner surface of the trocar 501. Typically the length is between 30 mm and 65 mm. By reducing the distance the distance to be traveled by the aerosol within the narrow trocar insert the quantity of aerosol exiting the trocar is increased.

Figures 39, 39A:
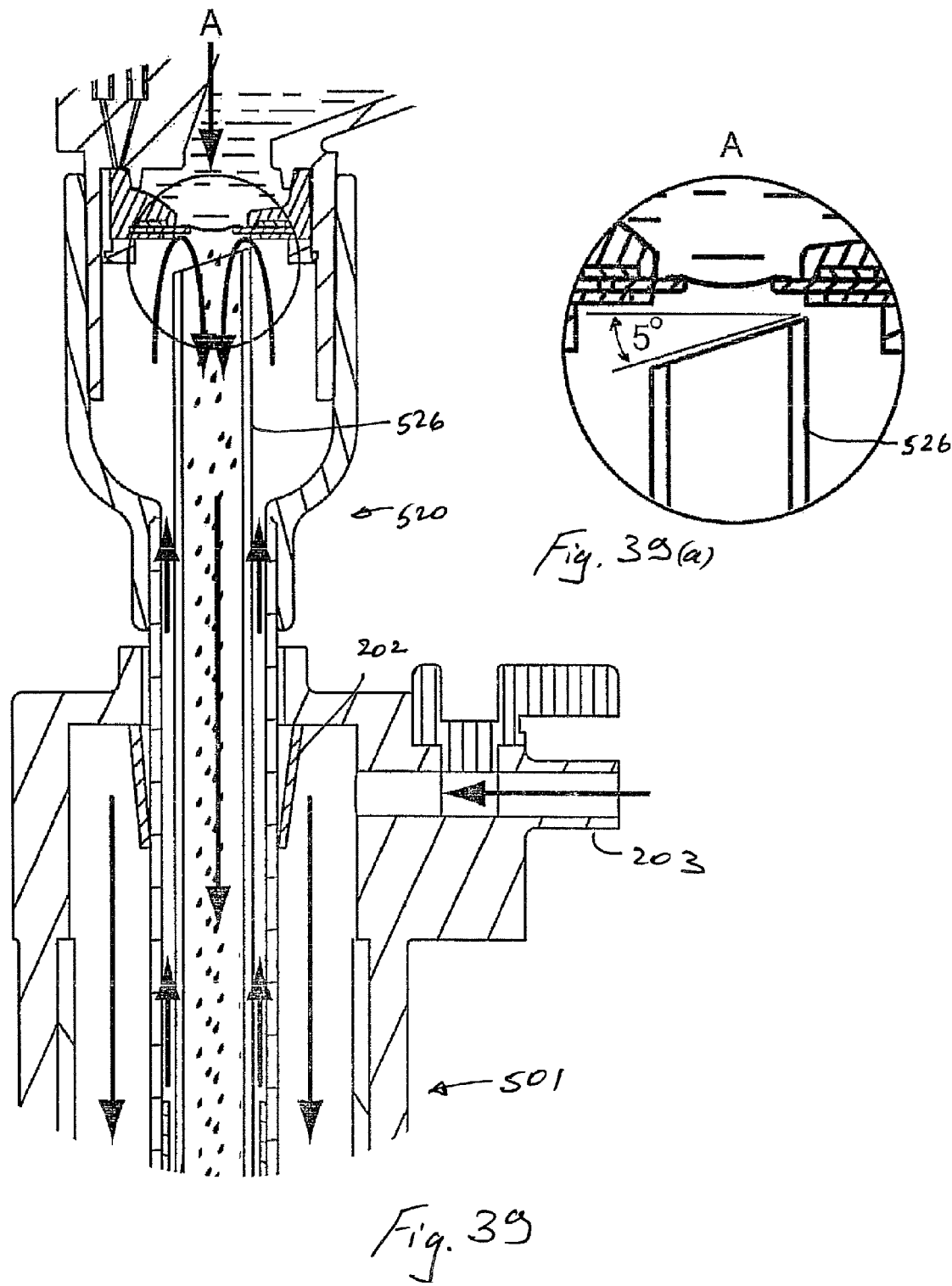
FIG. 39 is an elevational view of another apparatus in accordance with the present invention.
FIG. 39(a) is an enlarged view of a detail of FIG. 39.
Figure 40:
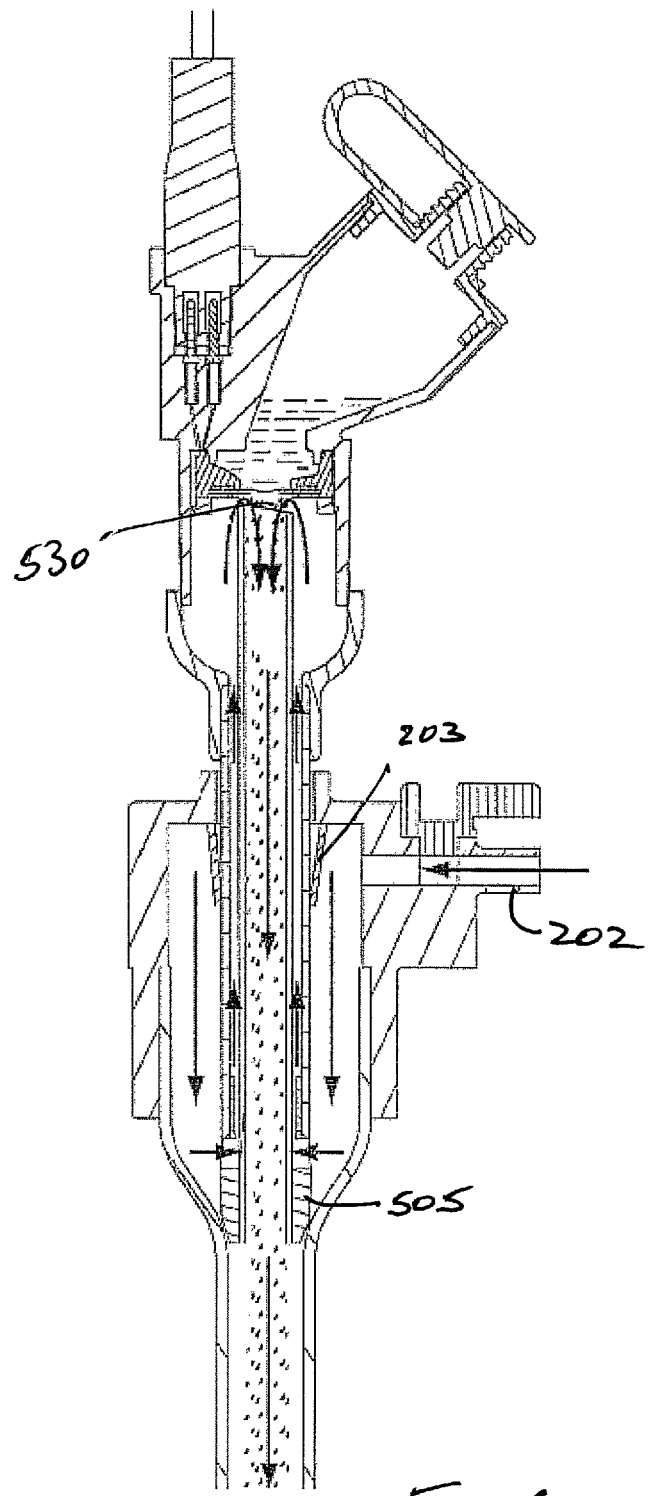
FIG. 40 is an enlarged view of detail A of the apparatus of FIG. 39.
Figure 41:
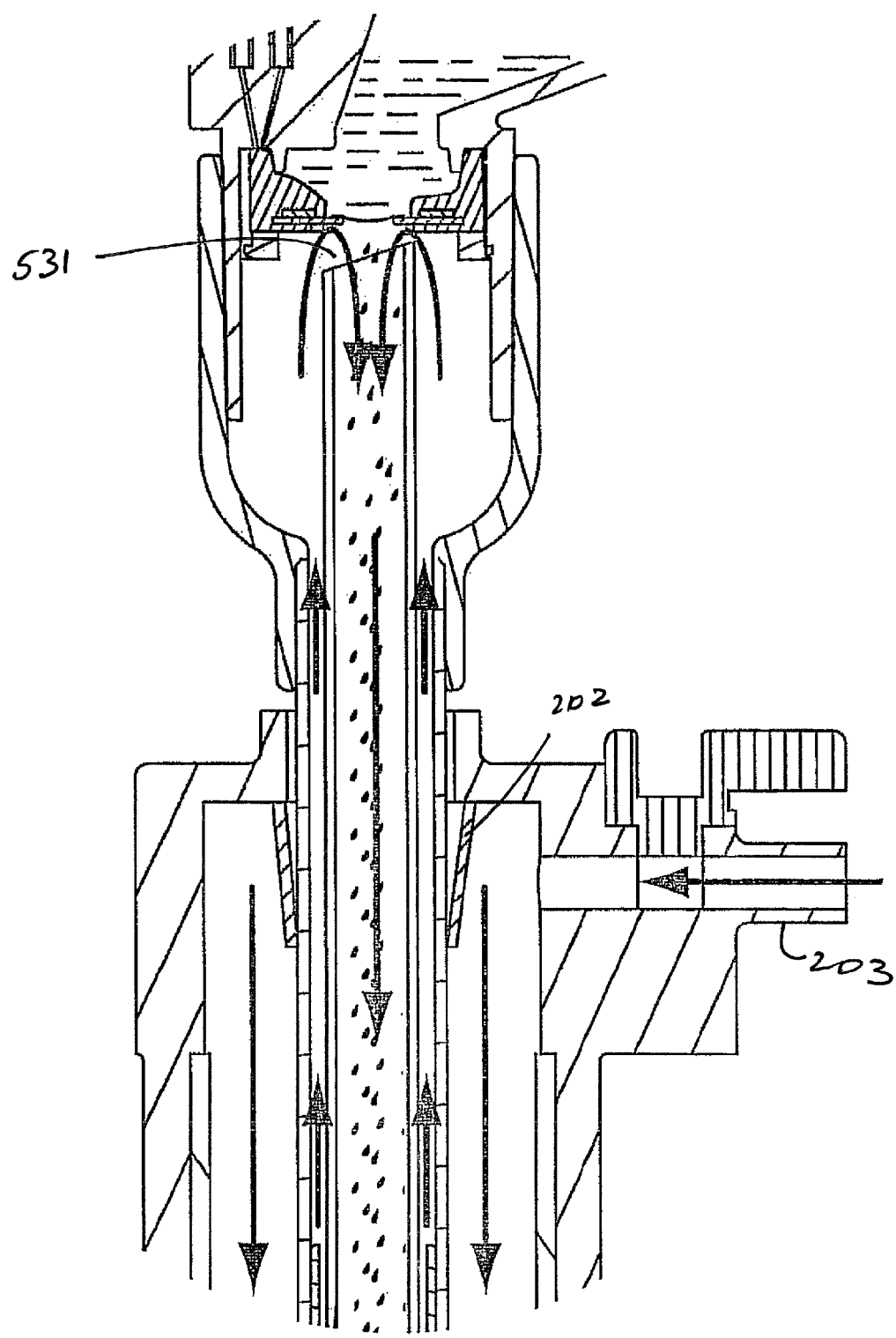
FIG. 41 is an elevational view of another apparatus in accordance with the present invention.
Figures 42, 42A:
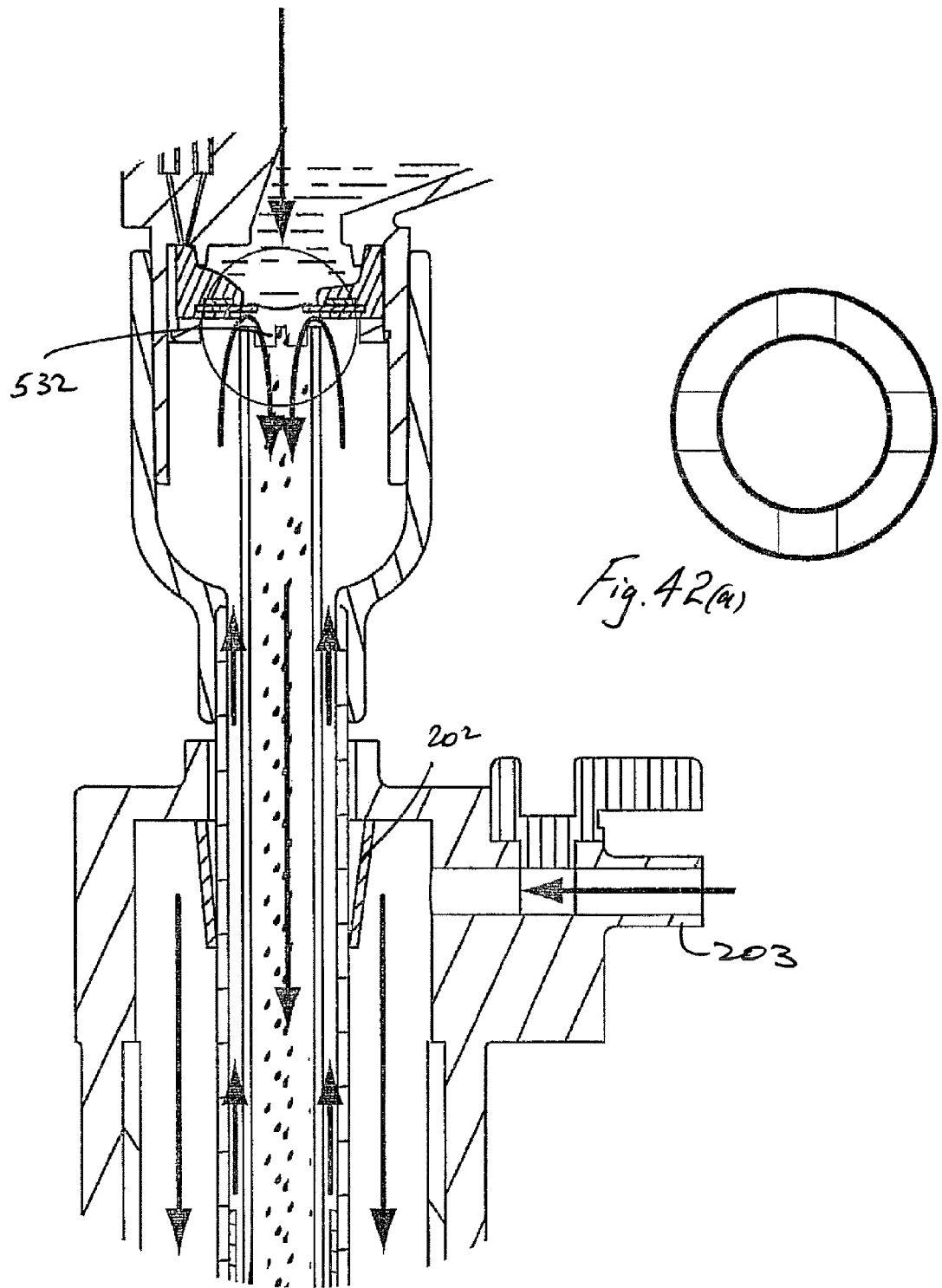
FIG. 42 is an elevational view of a further apparatus in accordance with the present invention.
FIG. 42(a) is an enlarged plan view of a detail of FIG. 42.
Figures 43, 43A:
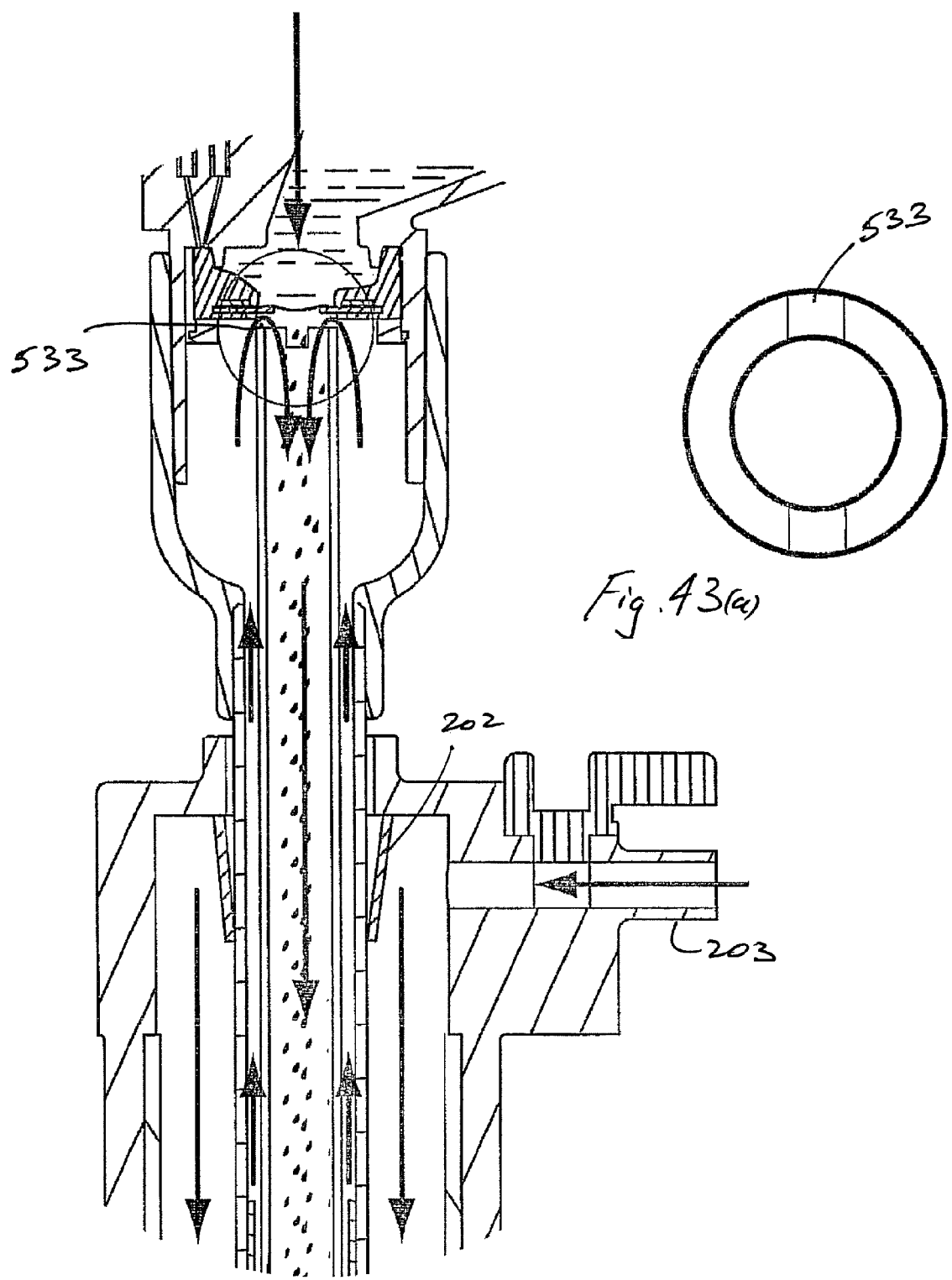
FIG. 43 is an elevational view of another apparatus in accordance with the present invention.
FIG. 43(a) is an enlarged plan view of a detail of FIG. 43.
Figures 44, 45:
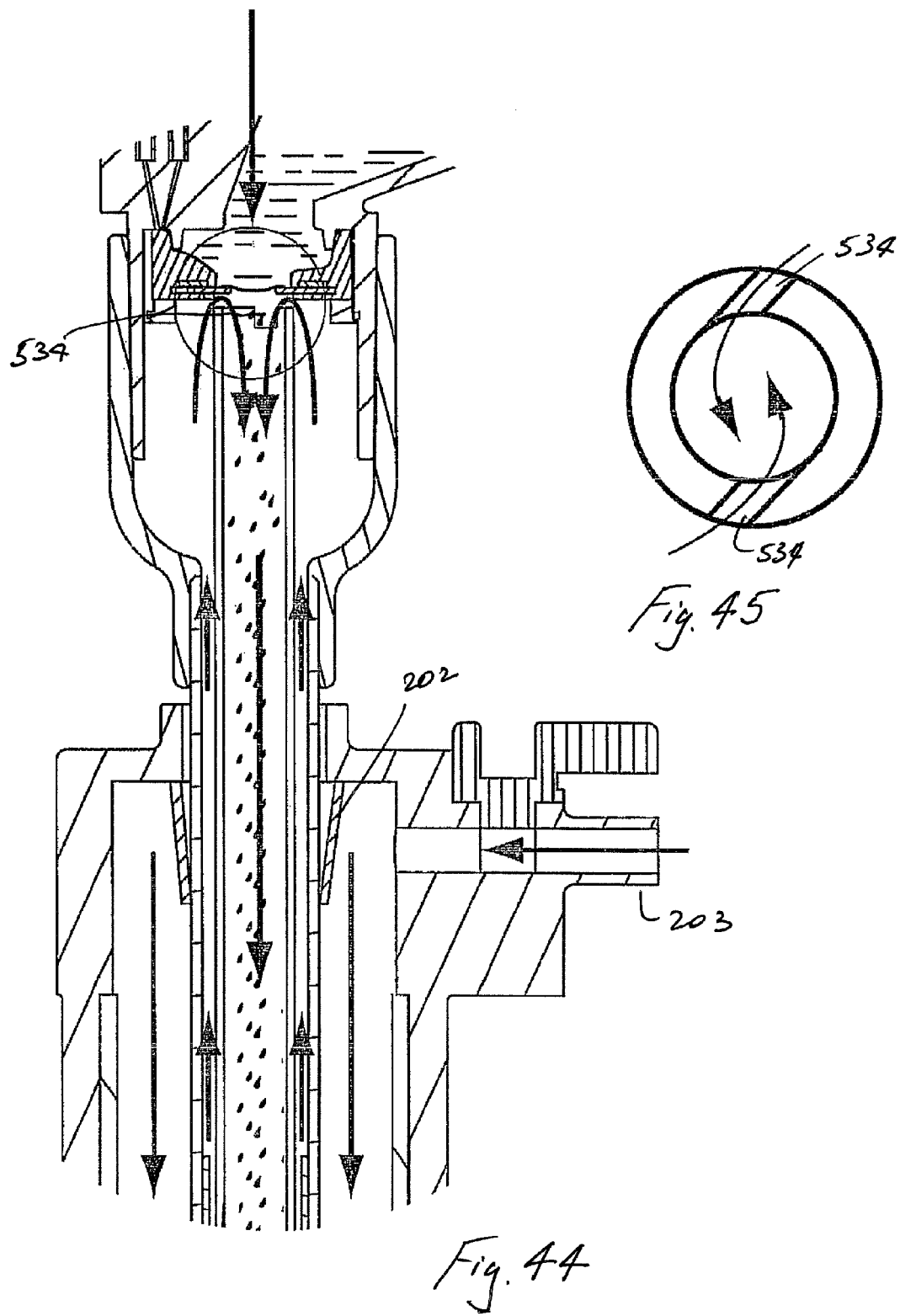
FIG. 44 is an elevational view of a further apparatus in accordance with the present invention.
FIG. 45 is a plan view of a detail of FIG. 44 illustrating a gas flow path.

Referring also to FIGS. 39 and 39(a) an inner tube 526 of a trocar insert may be extended to a position close to the underside of an aerosol generator 527. In this case there is a cut angle across the top of the inner tube which may, for example, be at about 5° so as to maximize entrainment of the aerosol with the gas so as to minimize losses in the inner tube from rainout due to wall contact. Thus, losses of aerosol in the insert is reduced. This system has the benefit of channeling the flow of generated aerosol for delivery to a patient. Some or all of these features may be used with any length of trocar insert. For example, it may be used in association with a short insert. Many different arrangements are possible such as those illustrated in FIGS. 40 to 45. There may be a small gap 530 which may be tapered (FIG. 40), a tapered interface 531 (FIG. 41), an interface with castellations 532 (FIG. 42), a single gas slit 533 (FIG. 43), or dual offset slits 534 (FIG. 44) to promote vortex formation as illustrated in FIG. 45.

Figure 46:
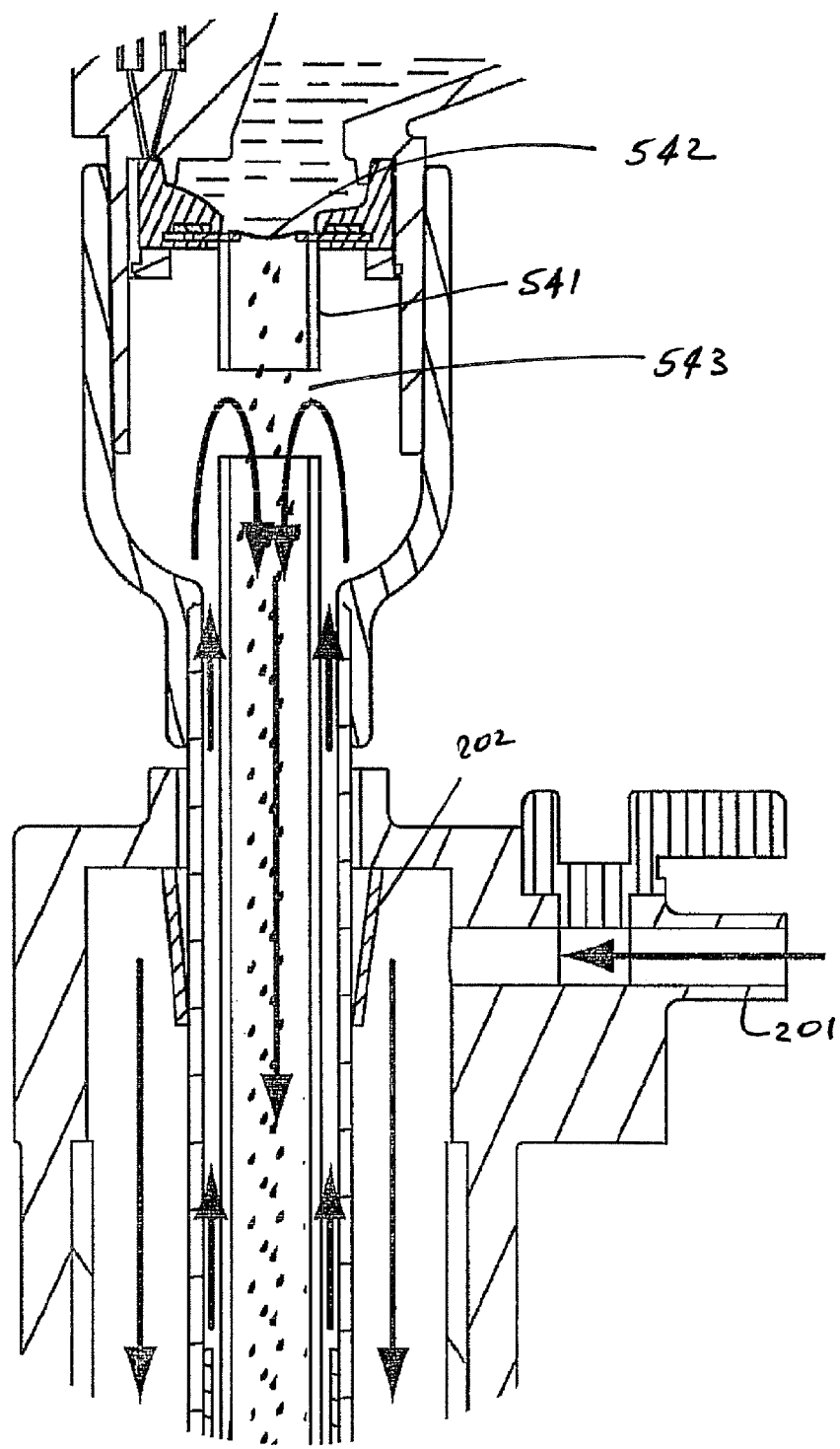
FIG. 46 is an elevational view of another apparatus in accordance with the present invention.

Referring to FIG. 46 there is illustrated an example of an aerosol insert 540 with a modified interface between a proximal end of an inner tube 541 of the insert and an aerosol generator 542. In this case the inner tube 541 comes into contact with the aerosol generator 542 and the inner tube has an inlet 543 for insufflation gas which is spaced below the proximal end of the inner tube 541. This modifies the aerosol flow dynamics for improved aerosol delivery efficiency.

Figure 47:
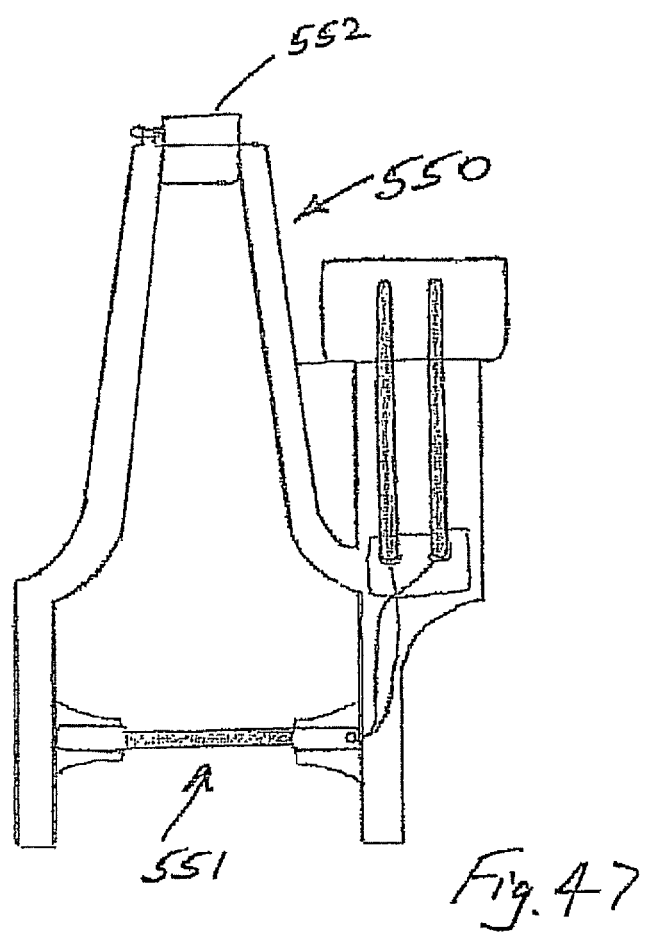
FIG. 47 is an elevational view of an apparatus in accordance with the present invention.

A liquid reservoir for the aerosol generator may be modified to facilitate efficient nebulization through a wide range of angles of orientation such as would be encountered in use during laparoscopic surgery. One example is illustrated in FIG. 47 in which a reservoir 550 is tapered. The reservoir 550 may be fitted with a removable plug 552. The plug may, for example, be of silicon.

Figure 48:
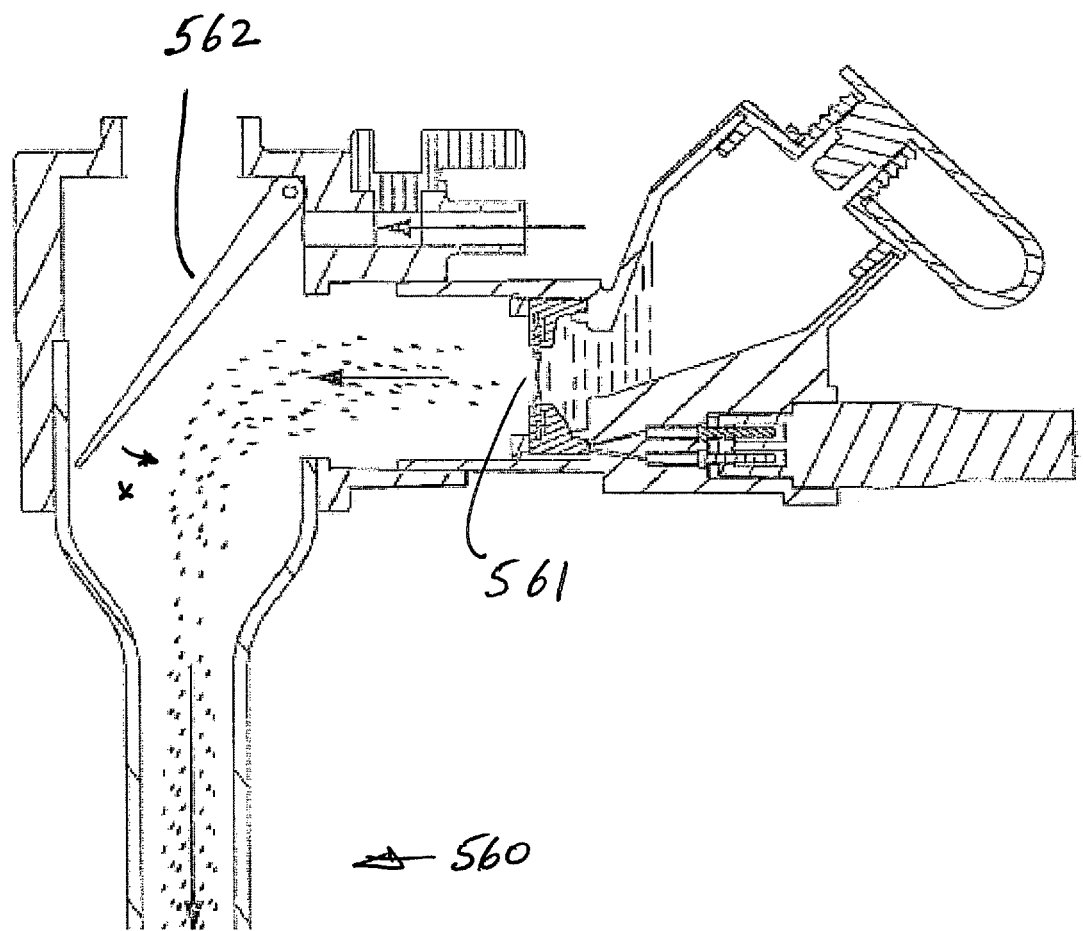
FIG. 48 is an elevational view of a further apparatus in accordance with the present invention.

Referring to FIG. 48 a trocar insert 560 of the present invention having an aerosol generator 561 may include a valve 562 such as a flap valve to facilitate the insertion of an instrument such as a trocar blade or obdurator. As the instrument is inserted, the flap valve 562 moves over in the direction of the arrow X to protect the aerosol generator 561. When the instrument is not present the flap 562 returns to a rest position and assists in directing the flow of aerosol generated by the aerosol generator down the shaft of the trocar.

Modifications and additions can be made to the embodiments of the present invention described herein without deporting from the scope of the present invention. For example, while the embodiments described herein refer to particular features, the present invention includes embodiments having different combinations of features. The present invention also includes embodiments that do not include all of the specific features described. Moreover, the features of the particular examples and embodiments may be used in any combination.

The present invention is not limited to the embodiments hereinbefore described, with reference to the accompanying drawings, which may be varied in construction and detail.

What is claimed is:

1. An apparatus for use in procedures involving insufflation, comprising:
   an aerosol generator for aerosolizing a fluid into an aerosol;

a trocar for delivery of the aerosol, the trocar comprising a housing to which the aerosol generator is mounted, the trocar having a proximal entry port for an insufflation gas and a distal end through which the aerosol is delivered; and an aerosol delivery tube extending from the aerosol generator into the trocar housing, the aerosol delivery tube having an aerosol outlet located distally with respect to the proximal entry port of the trocar.

2. The apparatus of claim 1, wherein a proximal end of the aerosol delivery tube is located adjacent to the aerosol generator.

3. The apparatus of claim 2, wherein the apparatus is adapted to direct the insufflation gas from the proximal entry port of the trocar to the proximal end of the aerosol delivery tube for entraining the aerosol in the insufflation gas and delivery of the insufflation gas and entrained aerosol through the trocar.

4. The apparatus of claim 3, wherein a gap is provided between the aerosol delivery tube and the aerosol generator for delivery of the insufflation gas into the aerosol delivery tube at the proximal end of the aerosol delivery tube.

5. The apparatus of claim 4, wherein the gap is defined by an angled cut at the proximal end of the aerosol delivery tube.

6. The apparatus of claim 5, wherein the angled cut is less than 20°.

7. The apparatus of claim 5, wherein the angled cut is less than 15°.

8. The apparatus of claim 5, wherein the angled cut is less than 10°.

9. The apparatus of claim 5, wherein the angled cut is approximately 5°.

10. The apparatus of claim 3, further comprising a proximal seal between the trocar and the aerosol delivery tube.

11. The apparatus of claim 3, wherein the aerosol delivery tube comprises an inner tube radially spaced apart from an outer tube to define an insufflation gas flow path between the inner tube and the outer tube.

12. The apparatus of claim 11, further comprising a distal seal between the outer tube and the trocar.

13. The apparatus of claim 1, further comprising a controller configured to control the operation of the aerosol generator.

14. The apparatus of claim 13, wherein the controller is remote from the trocar.

15. The apparatus of claim 13, wherein the controller is mounted to the trocar.

16. The apparatus of claim 13, wherein the controller is mountable to the trocar.

17. The apparatus of claim 13, wherein the controller is releasably mounted to the trocar.

18. The apparatus of claim 13, wherein the controller is configured to control a flow rate of the fluid to be aerosolized.

19. The apparatus of claim 13, wherein the controller is configured to deliver different flow rates of aerosol at different stages of a surgical procedure.

20. The apparatus of claim 13, wherein the controller is set to deliver a pre-set amount of aerosol into the insufflation gas.

21. The apparatus of claim 13, wherein the controller is configured to control operation of the aerosol generator responsive to the insufflation gas.

22. The apparatus of claim 1, further comprising a control system configured to control the operation of the aerosol generator, the control system comprising a first controller local to the trocar and a second controller remote from the trocar.

* * * * *